United States Patent
Creaturo

(10) Patent No.: US 10,625,026 B2
(45) Date of Patent: Apr. 21, 2020

(54) FORCE ACTUATED INJECTION DEVICE

(71) Applicant: Parenteral Technologies, LLC, Siesta Key, FL (US)

(72) Inventor: Michael A. Creaturo, Siesta Key, FL (US)

(73) Assignee: Parenteral Technologies, LLC, Siesta Key, FL (US)

( * ) Notice: Subject to any disclaimer, the term of this patent is extended or adjusted under 35 U.S.C. 154(b) by 600 days.

(21) Appl. No.: 15/200,298

(22) Filed: Jul. 1, 2016

(65) Prior Publication Data

US 2016/0310672 A1 Oct. 27, 2016

Related U.S. Application Data

(63) Continuation-in-part of application No. 14/601,420, filed on Jan. 21, 2015.

(60) Provisional application No. 61/929,768, filed on Jan. 21, 2014.

(51) Int. Cl.
*A61M 5/315* (2006.01)
*A61M 5/32* (2006.01)
*A61M 5/31* (2006.01)
*A61M 5/46* (2006.01)

(52) U.S. Cl.
CPC ...... *A61M 5/3158* (2013.01); *A61M 5/31511* (2013.01); *A61M 5/31555* (2013.01); *A61M 5/3287* (2013.01); *A61M 5/46* (2013.01); *A61M 5/31501* (2013.01); *A61M 2005/3114* (2013.01); *A61M 2005/3126* (2013.01);
(Continued)

(58) Field of Classification Search
CPC ........ A61M 5/28; A61M 5/281; A61M 5/283; A61M 5/31501; A61M 5/31505; A61M 5/31511; A61M 5/31515; A61M 5/31565; A61M 5/31578; A61M 5/3158; A61M 5/46; A61M 2005/31506; A61M 2005/31508; A61M 2005/3151; A61M 5/31591; A61M 5/3243; A61M 5/3271; A61M 2005/208; A61M 2005/31518
See application file for complete search history.

(56) References Cited

U.S. PATENT DOCUMENTS

| 4,927,416 A * | 5/1990 | Tomkiel ............... A61M 5/315 604/198 |
| 5,267,972 A | 12/1993 | Anderson |
| 7,500,963 B2 | 3/2009 | Westbye et al. |

(Continued)

OTHER PUBLICATIONS

International Search Report of corresponding International Application No. PCT/US15/12152; dated Apr. 9, 2015; 2 pages.

*Primary Examiner* — William R Carpenter
*Assistant Examiner* — Larry R. Wilson
(74) *Attorney, Agent, or Firm* — Clements Bernard Walker Law

(57) ABSTRACT

An injection device for holding and actuating a pre-filled syringe including a barrel holder having an axial passageway adapted to hold the barrel of the pre-filled syringe, a grip movable relative to the barrel holder to move a plunger of the pre-filled syringe, the grip configured to be locked to the barrel holder to prevent axial movement therebetween and unlocked from the barrel holder to permit axial movement therebetween, and a needle guard arranged to retract into the barrel holder in response to force against an injection site to unlock the grip from the barrel holder.

12 Claims, 36 Drawing Sheets

(52) U.S. Cl.
CPC ............... *A61M 2005/3139* (2013.01); *A61M 2005/3143* (2013.01); *A61M 2205/586* (2013.01)

(56) References Cited

U.S. PATENT DOCUMENTS

| | | |
|---|---|---|
| 8,337,472 B2 | 12/2012 | Edginton et al. |
| 8,591,463 B1 | 11/2013 | Cowe |
| 2008/0228147 A1 | 9/2008 | David-Hegerich et al. |
| 2009/0259178 A1 | 10/2009 | Brechbuchler et al. |
| 2011/0202011 A1 | 8/2011 | Wozencroft |
| 2012/0203186 A1* | 8/2012 | Vogt .................... A61M 5/3202 604/192 |
| 2012/0233834 A1 | 9/2012 | Szechinski et al. |
| 2013/0204229 A1* | 8/2013 | Olson ................ A61M 5/3213 604/506 |
| 2013/0237921 A1 | 9/2013 | Lannan et al. |
| 2013/0317480 A1 | 11/2013 | Reber et al. |
| 2017/0165429 A1* | 6/2017 | Holmqvist ........ A61M 5/31501 |

\* cited by examiner

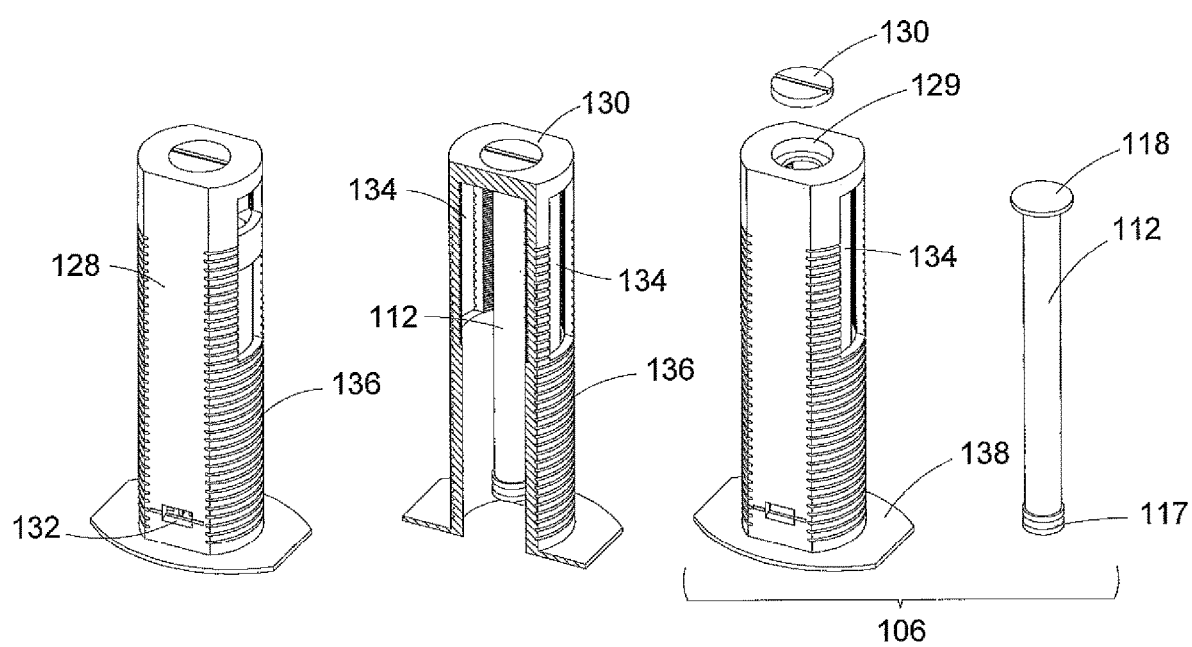

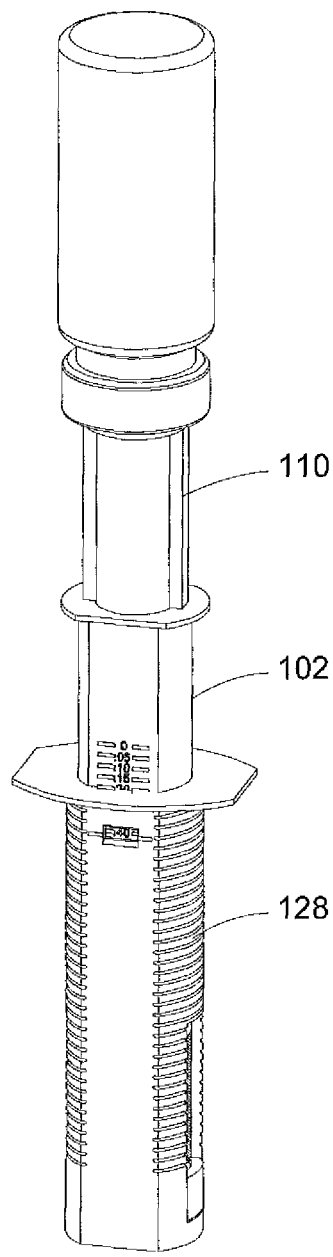 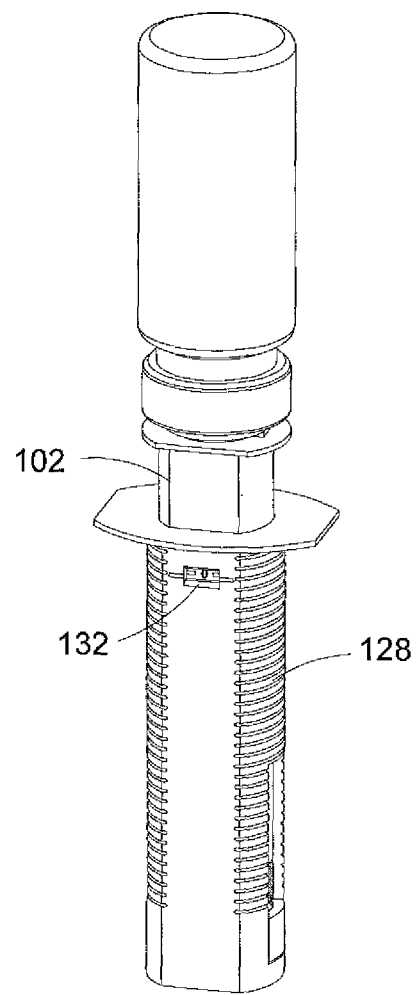
FIG. 15  FIG. 16

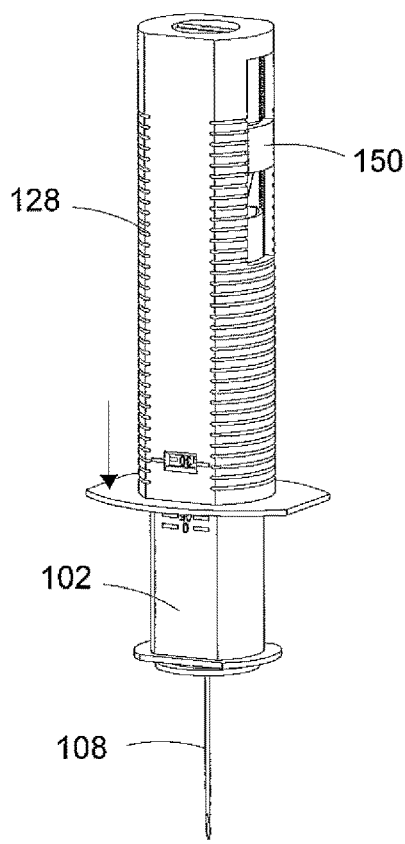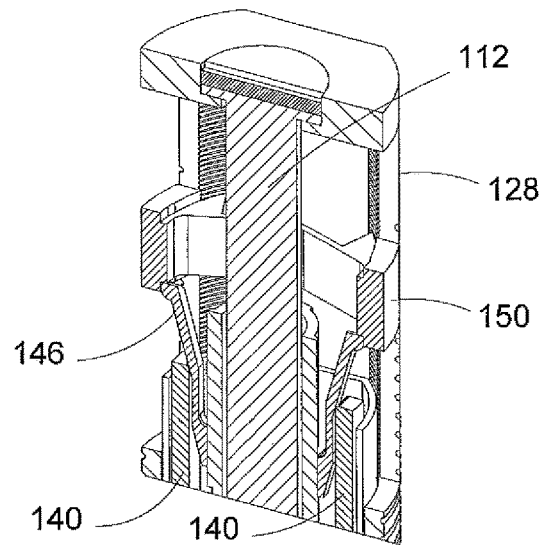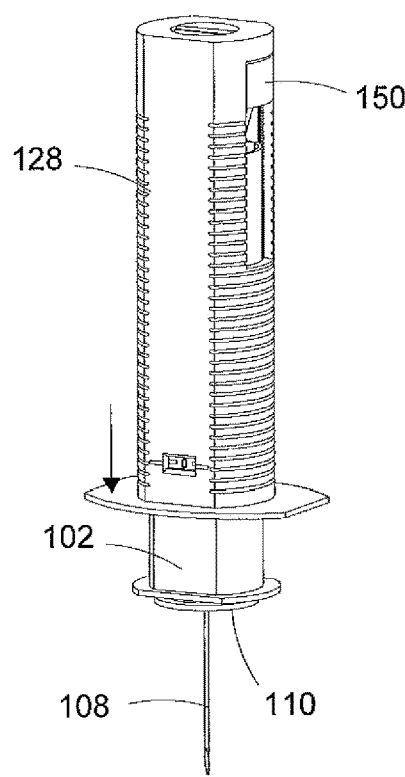
FIG. 20
FIG. 21
FIG. 22

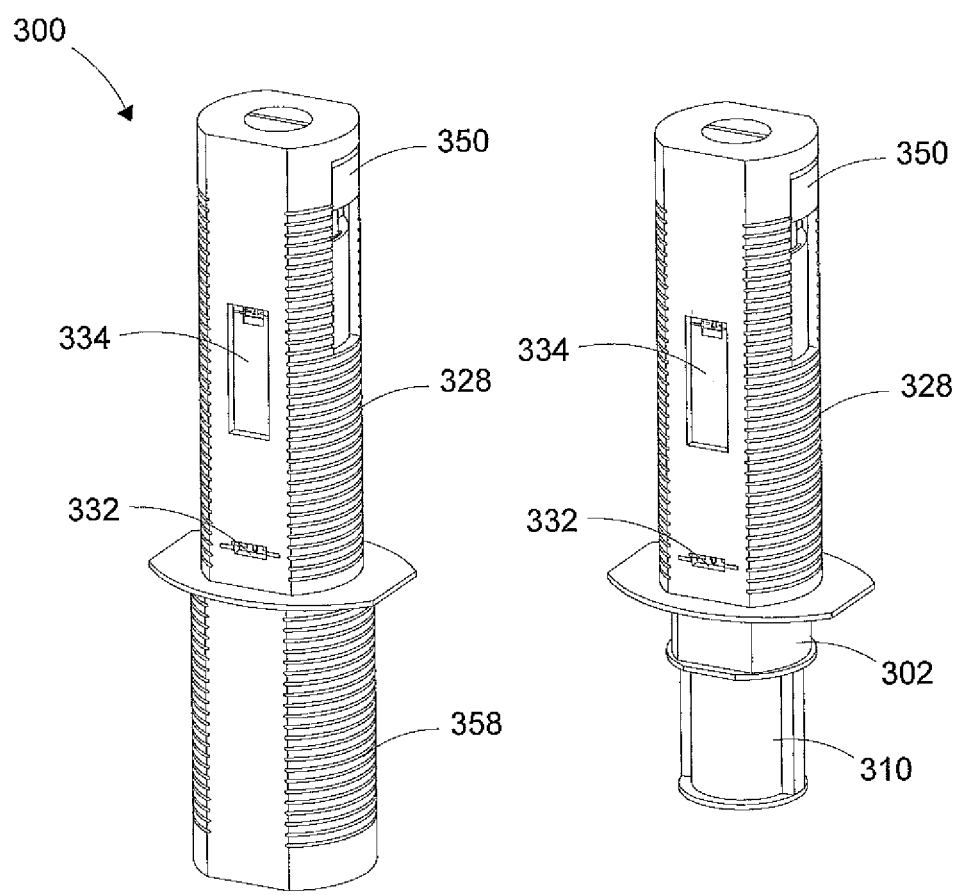
FIG. 32  FIG. 33

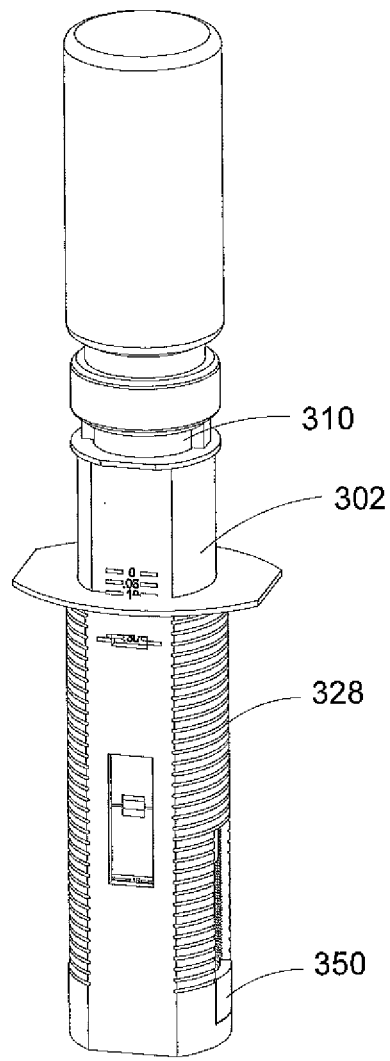 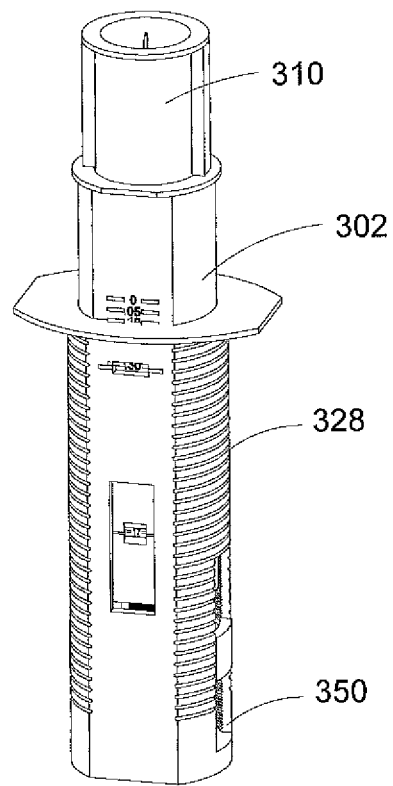
FIG. 36  FIG. 37
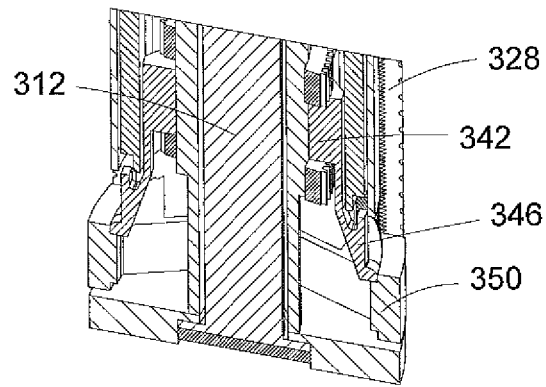
FIG. 38

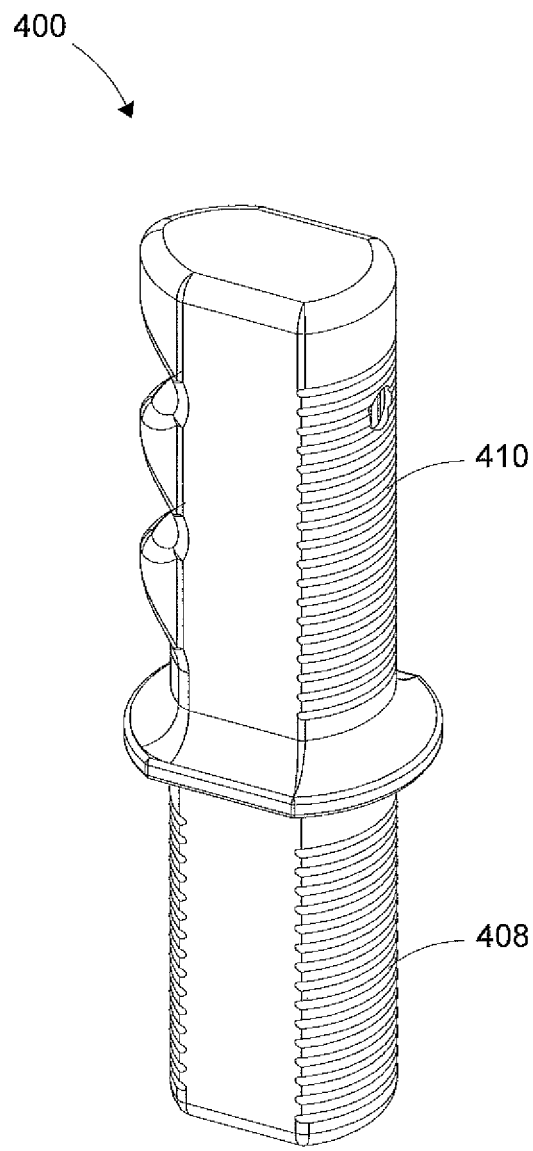
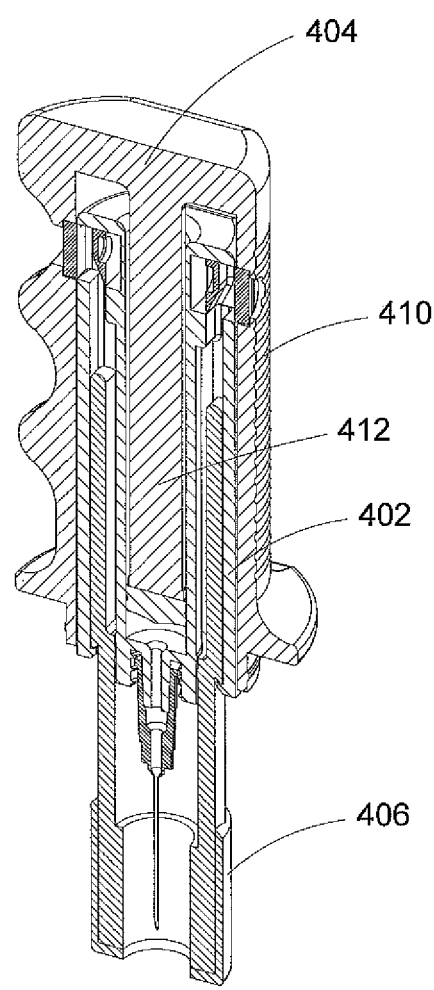
FIG. 57  FIG. 58

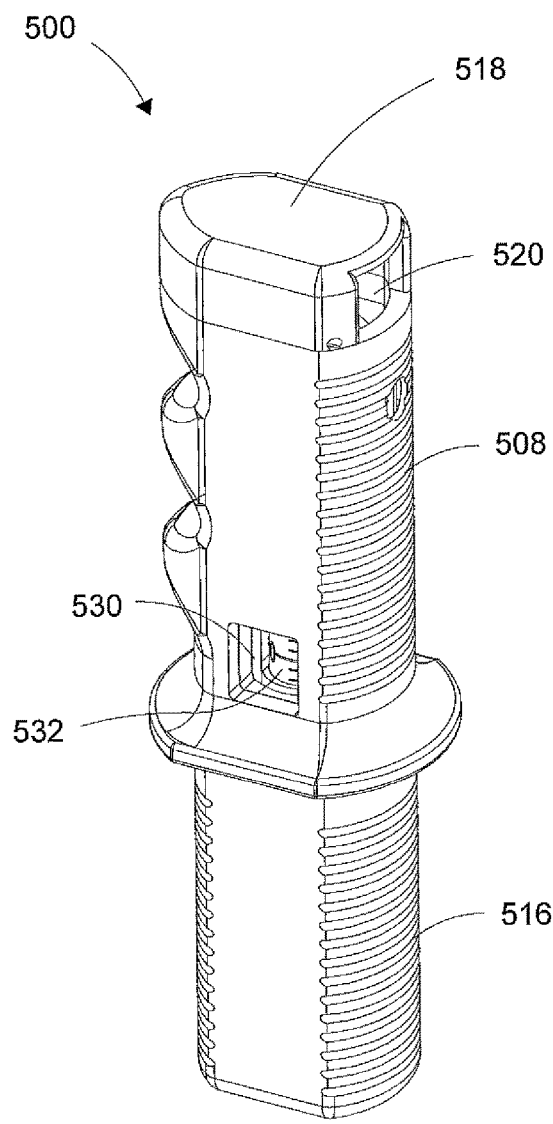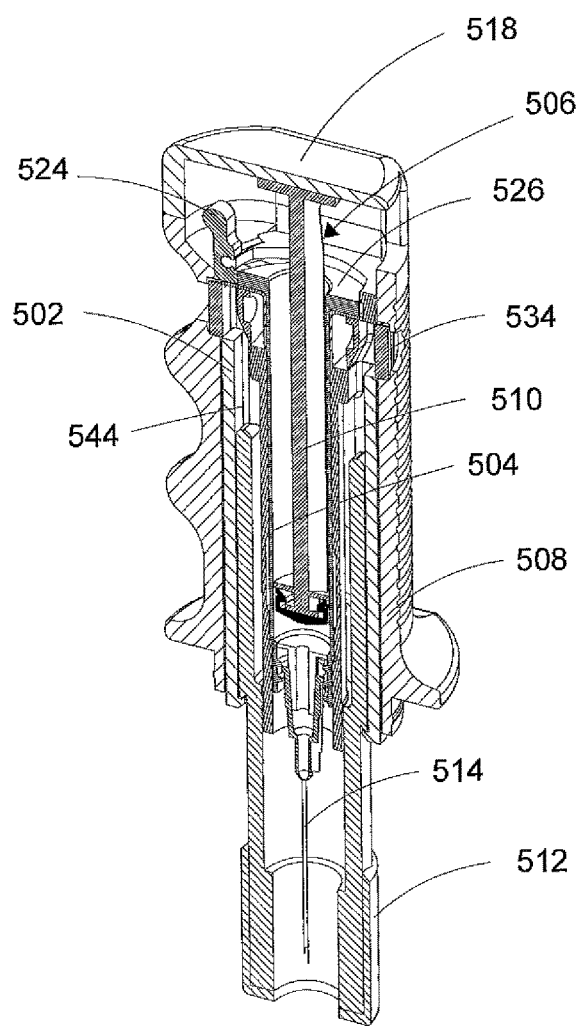
FIG. 66  FIG. 67

FORCE ACTUATED INJECTION DEVICE

CROSS-REFERENCE TO RELATED APPLICATIONS

This Continuation-in-Part application claims priority from U.S. application Ser. No. 14/601,420 filed Jan. 21, 2015, which claims priority from U.S. Application No. 61/929,768 filed Jan. 21, 2014, the entirety of which are incorporated by reference herein.

TECHNICAL FIELD AND BACKGROUND OF THE INVENTION

The present invention relates generally to an injection device for improving the speed, accuracy, safety and effectiveness of the administration of an emergency, life-saving injection during an anaphylactic event, and more particularly, to an injection device that operates by way of sequential manual actuation, wherein movement of a needle guard in response to pressure against the injection site initiates a hypodermic injection and triggers the release of a plunger for delivering medication from a reservoir, in one continuous motion.

Anaphylactic reactions are serious and sometimes fatal reactions to allergens, most commonly caused by food, drugs, insect stings, etc. Studies suggest that food allergies are increasing world-wide. According to a study released by the CDC, food allergies increased approximately 50% between 1997 and 2011. More than 17 million Europeans have a food allergy according to the European Academy of Allergy and Clinical Immunology. The CDC has also reported that food allergies result in more than 300,000 ambulatory care visits per year among children under the age of 18.

Auto-injectors are universally recommended as first-aid treatment for anaphylaxis. In a World Allergy Organization survey conducted in 2003, auto-injectors containing 0.3 mg of epinephrine were reported to be available in 56.4% of countries, and those containing 0.15 mg of epinephrine were reported to be available in 43.6% of countries. Auto-injectors containing an infant dose were not available in any country.

There have been many studies published about the inability of auto-injectors to effectively deliver epinephrine, particularly in pediatric patients. A first disadvantage of auto injectors is the ineffectiveness to deliver the accurate amount of epinephrine during an emergency anaphylaxis. Current epinephrine auto injectors are available in two standard doses: 0.15 mg and 0.3 mg, with the 0.15 mg dose for patients 30 kg and under, and the 0.30 mg dose for patients above 30 kg. According to The Journal of Allergy and Clinical Immunology, neither of these doses is appropriate for children weighing less than 10 Kg. A 20 kg child would have a similar issue in being under dosed with the 0.15 mg dose, and overdosed with the 0.30 mg dose. An overdose or under dose during a life threatening anaphylaxis, especially for a child or patient with small body mass, could be fatal.

A second disadvantage of auto injectors is the inability to effectively deliver the medication intramuscularly using one standard needle length. A study conducted at the Phoenix Children's Hospital found that the needle on epinephrine auto-injectors is not long enough to reach the muscle in a significant number of children. Another study presented during the 2013 Annual Meeting of the American Academy of Allergy, Asthma & Immunology (AAAAI) suggested that delivering epinephrine into the muscle allows for more rapid absorption and leads to higher blood levels than if injected into the overlying fat. Considering the rising obesity rates in children, there is concern that epinephrine auto-injectors will not adequately deliver the medication in overweight children who may be experiencing anaphylaxis. Without proper treatment, anaphylaxis can be fatal, therefore it is critical that epinephrine is administered quickly and effectively.

Additional studies have found that patient groups other than children are at risk of not receiving an adequate dose of epinephrine in an anaphylactic emergency. One study published in the American Journal of Emergency Medicine found that the current epinephrine auto injector needle length is inadequate for intramuscular injection, especially among women.

One study conducted at the University of Manitoba assessed absorption of epinephrine when injected subcutaneously and intramuscularly in children. The data showed subcutaneous injections reached the mean maximum plasma concentration at a range of 5 to 120 minutes. Patients injected intramuscularly reached a mean maximum plasma concentration in 8+/−2 minutes. This study supports the conclusion that, in children, recommendations for subcutaneous epinephrine injection are based on anecdotal experience, and should be reevaluated in view of the finding of delayed epinephrine absorption when this route is used. This delay may have important clinical implications during an episode of systemic anaphylaxis. Thus, the intramuscular route of injection is preferable. According to the National Institute of Allergy and Infectious Disease, if epinephrine is not given promptly, rapid decline and death could occur within 30 to 60 minutes. These findings clearly illustrate the need for patients experiencing anaphylactic shock to receive rapid intramuscular injections of epinephrine.

A third disadvantage of auto injectors is the high cost, which particularly affects developing nations.

While vial and syringe combinations for epinephrine administration have the advantage of being economical, they are cumbersome to carry on a daily basis, time-consuming to load and administer, and most importantly, open the door to dosage errors. Patients requiring self-administration are typically not capable of loading a syringe and administering the correct dosage during an anaphylactic event.

Therefore, what is needed is an economical alternative for administering injections during an anaphylactic event that overcomes the disadvantages of prior art injectors.

BRIEF SUMMARY OF THE INVENTION

It is an object of the invention to provide an injection device configured to deliver an accurate, personalized, rapid injection of a critical care life-saving dosage of epinephrine when speed, dosage accuracy and proper intramuscular delivery during an anaphylactic event are critical, particularly in children and other small body mass patients.

It is another object of the invention to provide an injection device calibrated to a patient's weight and/or Body Mass Index (BMI) in order to administer a precise dosage with the most operative needle length to improve the speed, accuracy, safety and effectiveness of the administration of a critical care injection such as epinephrine, or other medication.

It is another object of the invention to provide an injection device that is cost-effective and easy to use.

It is another object of the invention to provide an injection device configured to administer an injection in one continuous motion using the energy from the force of injection, and not stored energy within the device.

It is another object of the invention to provide an injection device that operates by way of sequential "stages" in one continuous motion to administer a medical injection from the force of applied pressure against the injection site.

It is another object of the invention to provide an injection device in which a predetermined amount of pressure against the injection site initiates the device to, in sequence, puncture the injection site, penetrate hypodermically to a patient specific depth, and deliver a patient specific dosage from within the reservoir of the device.

It is another object of the invention to provide an injection device configured to deliver an injection by way of momentum initiated by the retraction or other actuation of the needle guard or like component of the device applied by force against the injection site.

It is another object of the invention to provide an injection device for administering a medicinal injection that operates by utilizing momentum from the force of injection to deliver the medication.

To achieve the foregoing and other objects and advantages, in a first embodiment provided herein is an injection device including a barrel holder having an axial passageway adapted to hold a barrel of a pre-filled syringe, a grip slidably disposed over the barrel holder and adapted to engage a plunger of the pre-filled syringe, the grip configured to lock to the barrel holder to prevent axial movement therebetween and unlock from the barrel holder to allow axial movement therebetween to drive axial movement of the plunger relative to the barrel, and a needle guard configured to partially retract into the barrel holder in response to force against an injection site to unlock the grip from the barrel holder.

In a further aspect, the grip can have a removable cap at one end thereof adapted to engage an end of the plunger, the removable cap having an opening through a sidewall thereof for allowing the removable cap to slide over the end of the plunger when installing the removable cap on the grip.

In a further aspect, the injection device can have a barrel lock at one end of the barrel holder configured to lock the barrel to the barrel holder.

In a further aspect, the barrel holder can have a recess at one end thereof adapted to receive a finger flange of the pre-filled syringe, and a rail laterally adjacent the recess, wherein the barrel lock is configured to engage the finger flange and is slidable along the rail to rotate the finger flange relative to the barrel holder to compress the finger flange to lock the barrel to the barrel holder.

In a further aspect, the barrel holder can have a window through a sidewall thereof for viewing indicia or fluid of the pre-filled syringe.

In a further aspect, the injection device can include grip locks disposed in openings through sidewalls of the barrel holder, the grip locks arranged to contact the grip to lock the grip to the barrel holder and move out of contact with the grip in response to contact with the needle guard to unlock the grip from the barrel holder.

In a further aspect, the grip locks can be biased in a direction outward away from the barrel holder.

In a further aspect, the injection device can include a biasing member disposed between the barrel holder and the needle guard arranged to bias the needle guard away from the barrel holder.

In a further aspect, the injection device can include a removable cover attached to one end of the grip.

In a further aspect, the needle guard can include a cylindrical body having a pair of diametrically opposed arms extending axially from one end of the cylindrical body in a direction of the grip, wherein as the needle guard retracts into the barrel holder a predetermined distance the arms urging the grip locks inward out of contact with the grip to unlock the grip from the barrel holder to permit axial movement therebetween.

In a further aspect, the arms can be guided along elongate channels within the barrel holder.

In a further aspect, the injection device is momentum driven in that force against the injection site causes the needle guard to retract into the barrel holder a predetermined distance to unlock the grip from the barrel holder to allow the grip to move in a direction of the injection site to advance the plunger in the barrel to deliver a dosage of predetermined medication in one continuous motion.

In a further aspect, the injection device can include a needle depth adjustment mechanism associated with the barrel and including a rotating dial for adjusting a position of the barrel relative to the barrel holder to adjust needle depth.

According to another embodiment of the invention, the present invention provides an injection device for actuating a pre-filled syringe including a barrel holder having an axial passageway adapted to hold a barrel of the pre-filled syringe, a grip movable relative to the barrel holder to move a plunger of the pre-filled syringe, the grip configured to be locked to the barrel holder to prevent axial movement therebetween and unlocked from the barrel holder to permit axial movement therebetween, and a needle guard arranged to retract into the barrel holder in response to force against an injection site to unlock the grip from the barrel holder.

Embodiments of the invention can include one or more or any combination of the above features, aspects and configurations.

Additional features, aspects and advantages of the invention will be set forth in the detailed description which follows, and in part will be readily apparent to those skilled in the art from that description or recognized by practicing the invention as described herein. It is to be understood that both the foregoing general description and the following detailed description present various embodiments of the invention, and are intended to provide an overview or framework for understanding the nature and character of the invention as claimed. The accompanying drawings are included to provide a further understanding of the invention, and are incorporated in and constitute a part of this specification.

BRIEF DESCRIPTION OF THE DRAWINGS

Features, aspects and advantages of the present invention are better understood when the following detailed description of the invention is read with reference to the accompanying drawings, in which:

FIG. 6 is an isometric view of the plunger assembly of the device of FIG. 1;

FIG. 7 is a cutaway view of the plunger assembly of FIG. 6;

FIG. 8 is an exploded view of the plunger assembly of FIG. 6;

FIG. 15 shows a medication vial aligned with the needle guard;

FIG. 16 shows the needle inserted into the vial;

FIG. 20 shows the device of FIG. 1 with the needle guard retracted and with the plunger in the starting position;

FIG. 21 is a detailed view illustrating movement of the needle guard triggering release of the plunger;

FIG. 22 shows the device of FIG. 1 with the needle guard retracted and the plunger fully depressed;

FIG. 32 is an isometric view of an injection device according to a third embodiment of the invention;

FIG. 33 shows the device of FIG. 32 with the safety cap removed and the plunger lock in the non-operative position;

FIG. 36 shows the device loaded with a predetermined dosage;

FIG. 37 shows the loaded device with the plunger lock in the operative position;

FIG. 38 is a detailed view of the plunger lock;

FIG. 57 is an isometric view of an injection device according to a fourth embodiment of the invention;

FIG. 58 is a longitudinal sectional view through the device of FIG. 57;

FIG. 66 is an isometric view of an injection device configured to hold a pre-filled syringe;

FIG. 67 is a vertical cross-section through the injection device of FIG. 65;

DETAILED DESCRIPTION OF THE INVENTION

Figure 1:
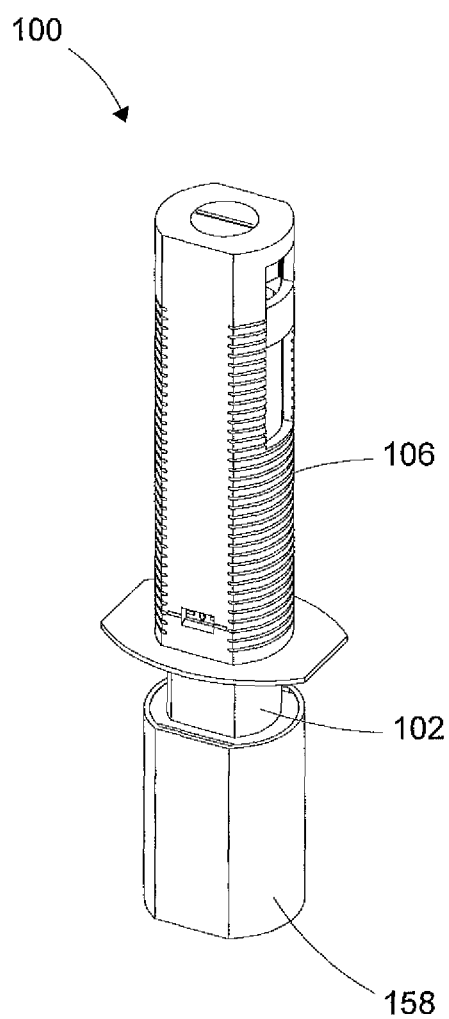
FIG. 1 is an isometric view of an injection device according to a first embodiment of the invention.
Figure 2:
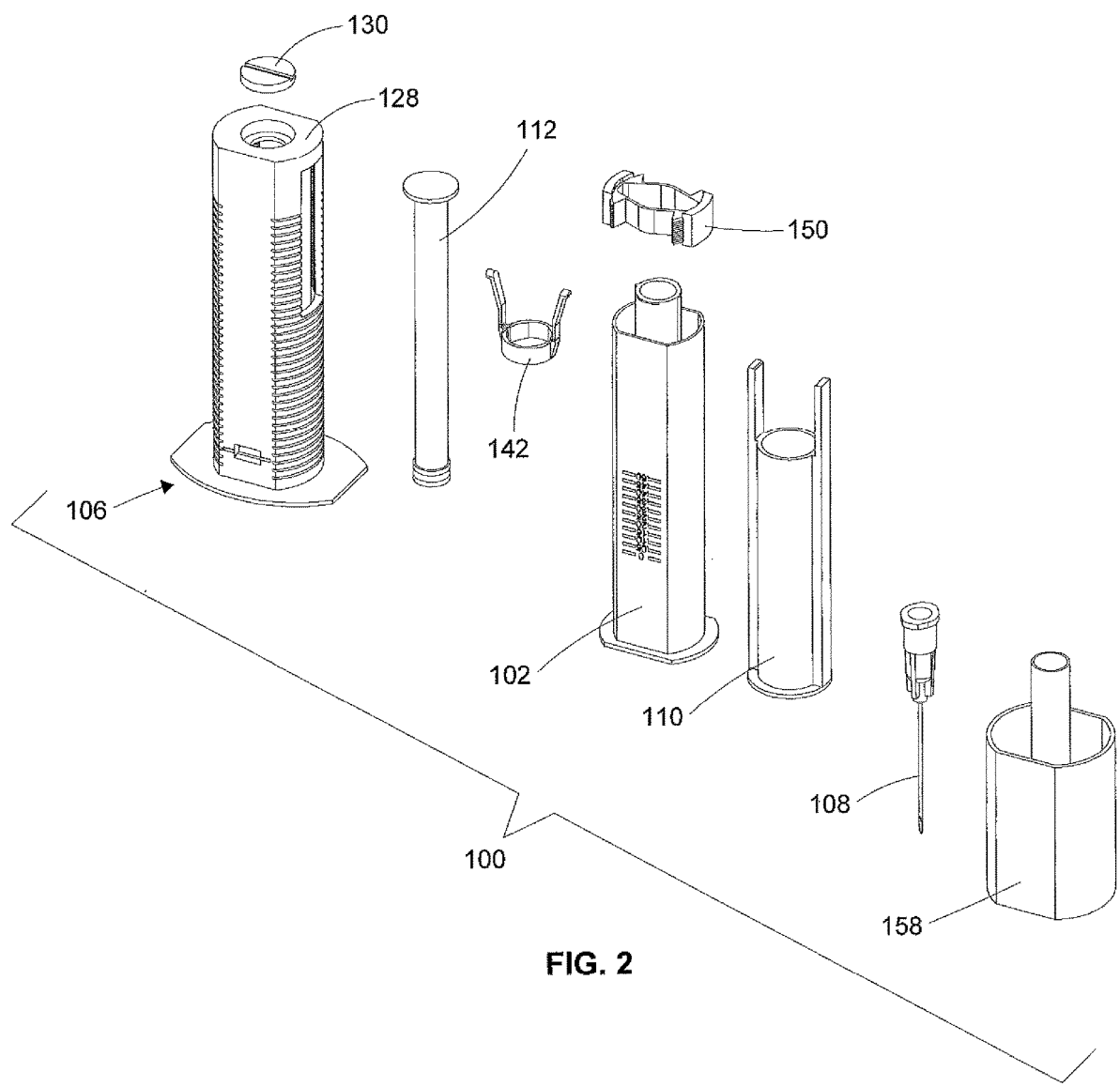
FIG. 2 is an exploded view of the device of FIG. 1.
Figure 3:
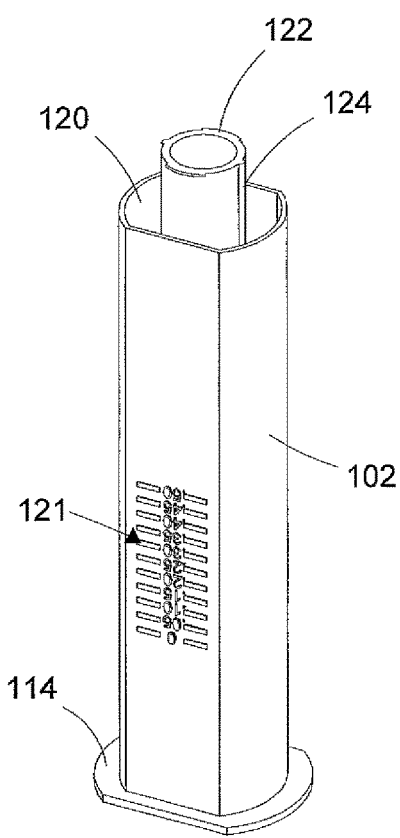
FIG. 3 is an isometric view of the barrel of the device of FIG. 1.
Figure 4:
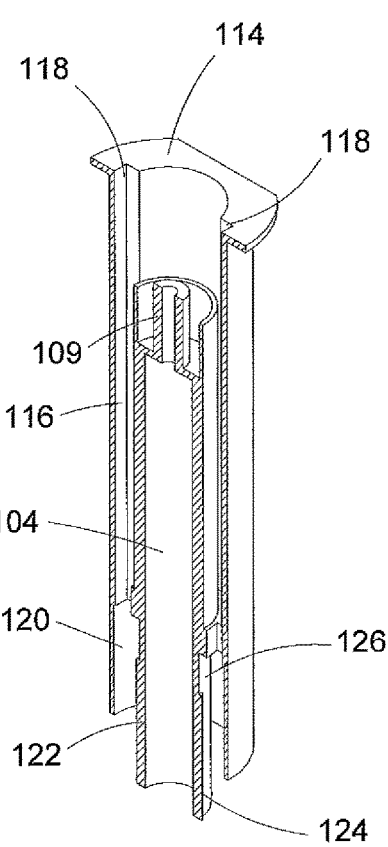
FIG. 4 is a longitudinal sectional view through the barrel of FIG. 3.
Figure 5:
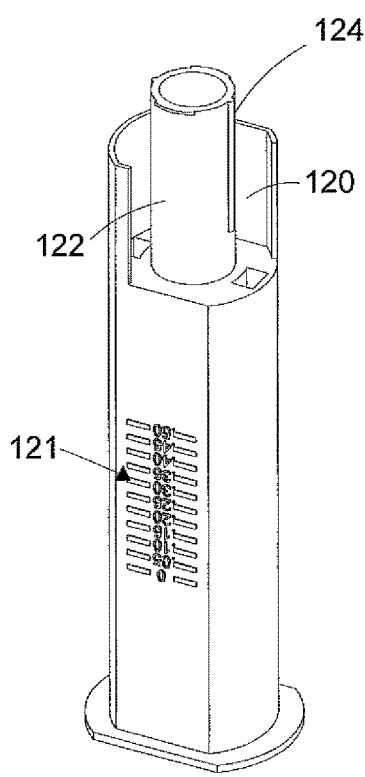
FIG. 5 is a cutaway view of the barrel of FIG. 3.
Figure 9:
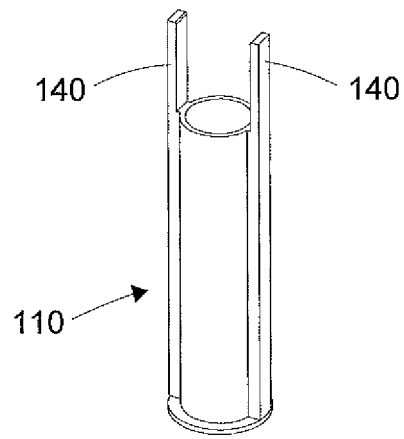
FIG. 9 is an isometric view of the needle guard of the device of FIG. 1.
Figure 10:
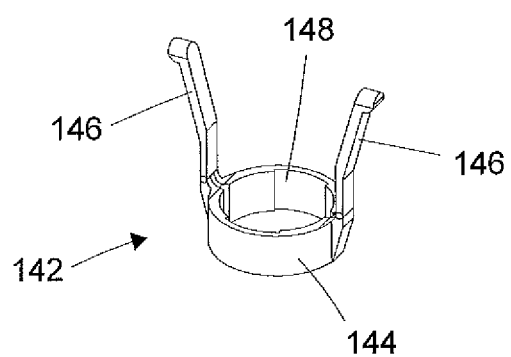
FIG. 10 is an isometric view of the plunger stop of the device of FIG. 1.
Figure 11:
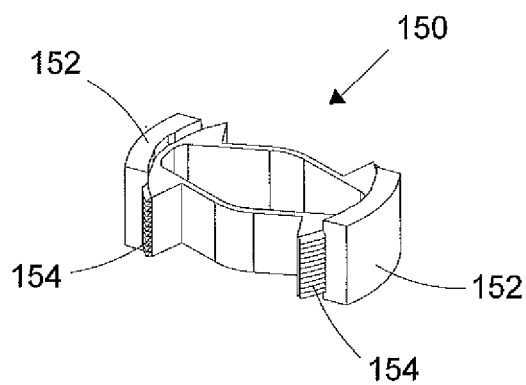
FIG. 11 is an isometric view of the plunger lock of the device of FIG. 1.
Figure 12:
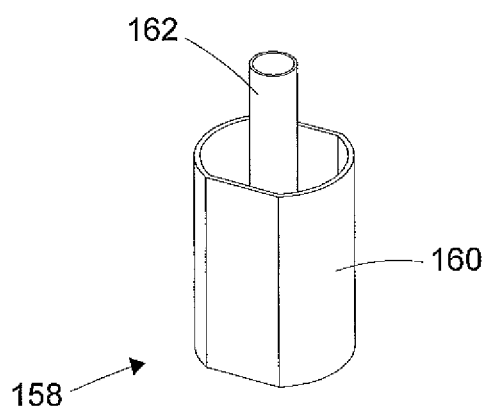
FIG. 12 is an isometric view of the removable safety cap of the device of FIG. 1.
Figure 13:
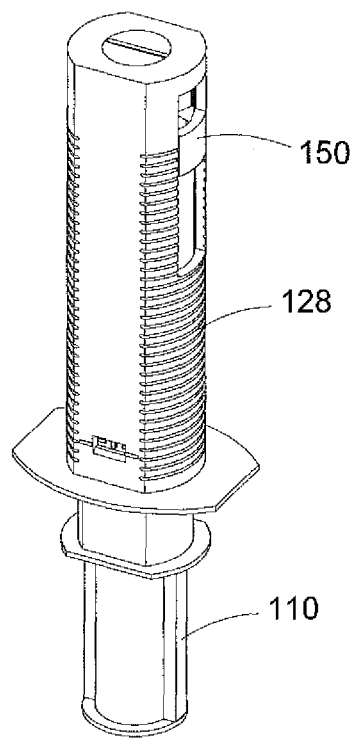
FIG. 13 is an isometric view of the device of FIG. 1 shown with the plunger lock in the non-operative position.
Figure 14:
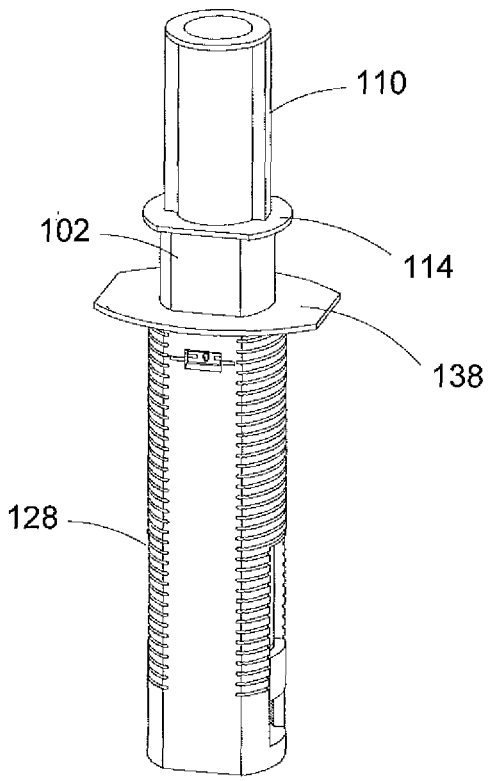
FIG. 14 is an isometric view of the device of FIG. 13 shown from another angle.

The present invention will now be described more fully hereinafter with reference to the accompanying drawings in which exemplary embodiments of the invention are shown. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention. Like reference numbers refer to like elements throughout the various drawings.

Referring to FIGS. 1-22, a first embodiment of an injection device for administering a dosage of epinephrine or other critical care injection, referred to generically herein as the "medication," is shown generally at reference numeral 100. Although the injection device shown and described herein utilizes a needle for delivering the medication, it is envisioned and intended that the features and configurations described herein may be adapted to and implemented with other types of injection devices for delivering medication hypodermically.

The injection device 100 generally includes a barrel 102, a plunger assembly 106, and a removable safety cap 158. The barrel defines an internal reservoir for containing a volume of medication, also referred to herein as the "dosage." The plunger assembly 106 is axially movable relative to the barrel 102 in a first direction to load the reservoir, and in the opposing direction to force the medication from the reservoir.

The injection device further includes a hypodermic needle 108 configured to attach to one end of the barrel, for example by way of a Luer-lock, to deliver the medication intramuscularly, subcutaneously, or another route, and a retractable needle guard 110 for guarding the needle and triggering the delivery mechanism of the injection device, as described below. The plunger assembly 106 generally includes a grip 128 that axially overlaps a portion of the barrel 102, and a plunger 112 configured to be fixed relative to the grip 128. The plunger 112 may be received through one end of the grip 128 by way of a removable cap 130. The cap 130 secures in place over one end of the plunger 112 to fix the inner plunger relative to the outer grip. In use, the grip 128 and plunger 112 move together axially relative to the barrel 102 to load and administer the medication. A plunger stop 142 is arranged to control axial movement of the plunger 112 relative to the barrel 102, and a plunger lock 150 functions to lock the axial position of the plunger assembly 106 relative to the barrel 102, for example, to set the dosage.

The barrel 102 is an elongate, generally cylindrical body defining an internal passageway therethrough. The hypodermic needle 108 attaches to one end of the barrel 102, and the opposing end of the barrel is open to receive the internal plunger 112 of the plunger assembly 106. An airtight seal is provided between one end of the plunger 112 and the inner wall of the barrel reservoir 104 such that the medication is forced from the reservoir through the hypodermic needle as the plunger is axially advanced into the barrel 102, and cannot pass between the plunger 112 and the reservoir wall. The barrel 102 has a generally cylindrical cross-section with diametrically opposed flat sides. The flat sides may serve to locate indicia 121, for example, volumetric indicia. Volumetric indicia may include, but is not limited to, mL, IU, CC, MG, MCG, etc. Indicia may also be provided in the form of KG, LB, Body Surface Area (BSA), Body Mass Index (BMI), etc.

The barrel 102 defines a lateral flange 114 adjacent the needle end to facilitate gripping and manipulating the barrel to introduce air into the reservoir. The barrel 102 defines an elongate annular passage 116 for receiving the retracting needle guard 110. The barrel 102 defines diametrically opposed guide channels 118 for aligning and guiding the needle guard 110 as the needle guard retracts into the barrel. An annular chamber 120 surrounds the end of the reservoir 104 opposite the needle end and receives the plunger stop 142. The end of the reservoir opposite the needle end terminates in an internal cylindrical stem 122 having diametrically opposed external rails 124 and optional external threading 126 around at least a portion of the circumference thereof, the rails and optional threading functioning, at least in part, to guide the plunger stop into place 142 and facilitate alignment of the plunger stop with the retracting needle guard 110.

The plunger assembly 106 generally includes the outer grip 128 and the internal plunger 112. The grip 128 has a cross-section similar to that of the barrel 102, albeit a larger diameter, such that a portion of the grip axially overlaps the barrel and rotation therebetween is prevented. The plunger 112 terminates at one end in a seal 117 and at the opposing end in an enlarged head 118 trapped between an annular flange of the grip 128 and the removable cap 130. The grip 128 defines one or more windows, with window 132 indicating the dosage and defined along a flat face of the grip corresponding in alignment with the underlying volumetric indicia on the barrel. Windows 134 are defined thru an arcuate portion of the grip 128 and are used to accessing and manipulate the plunger lock therethrough. The grip 128 may define exterior gripping features 136 to facilitate gripping. An enlarged lateral flange 138 functions as a palm rest during the injecting motion.

The needle guard 110 is a generally cylindrical body having diametrically opposed guide rails 140 extending axially from one end thereof. The needle guard 110 and plunger assembly are calibrated to resist a specific amount of force to actuate the needle guard "upwards" (i.e., in the direction of the barrel). The needle guard 110 "unlocks" the delivery mechanism upon the applied pressure from the injection site, which in turn allows the medication to be delivered. The needle guard 110 retracts within the barrel as the hypodermic needle advances into the patient. At the same time, the guide rails 140 are guided along the guide channels within the barrel. The needle guard 110 retracts as it comes into contact with the injection site from the force of the injection. The needle guard 110 may have a predetermined length thereby providing a predetermined amount of linear length between the needle guard end and the needle tip, thus allowing a calibrated amount of momentum to be in place for the needle tip to penetrate the patient. Prior to injection, the needle guard 110 also functions to conceal the needle and prevent accidental sticks. The needle guard 110 also desensitizes the injection site just prior to the needle puncturing the skin lessoning/reducing the initial pricking/pinching sensation felt by the patient. A relatively tight fit may be provided between the barrel 102 and the needle guard 110 such that a predetermined force is needed to move the needle guard relative to the barrel. With such a tight fit, the needle guard is not free to move simply by changing the orientation of the tool, but requires that the needle guard either come into contact with the injection site or is otherwise purposefully handled and moved (e.g., retracted or pulled).

The plunger stop 142, which sits within the annular chamber around the stem, generally includes an annular band 144 having diametrically opposed arms 146 that extend in the same direction away and outward from the band. The band defines inner channels 148 that align with the stem rails to align the plunger stop 142 relative to/on the stem. The arms 146 are resiliently deformable and biased radially outward such that when the needle guard 110 is not fully retracted the ends of the arms engage within a slot in the plunger lock to prevent axial movement of the plunger relative to the barrel, and are forced radially inward and out of engagement with the plunger lock when the needle guard is retracted, thereby allowing the plunger to move axially relative to the barrel to deliver the medication.

The plunger lock 150 functions to lock the axial position of the plunger assembly relative to the barrel, for example, to set the dosage. The plunger lock 150 includes diametrically opposed finger grips 152 that are accessible through the windows located along the sides of the grip. The plunger lock 150 may be made from a resiliently deformable material capable of being compressed radially inward in order to disengage teeth 154 from corresponding teeth located on the inner wall of the grip (see FIG. 18 at 156). The plunger lock 150 installs around the stem of the barrel, and the arms of the plunger stop rest against the end or a shoulder of the plunger lock 150 when the plunger lock is in the operative position, thus preventing axial movement between the plunger and barrel. As the arms 146 are urged radially inward in response to force from the retracting needle guard 110, the arms move out of engagement with and clear of the plunger lock 150, thereby allowing the plunger assembly to move axially in the direction of the barrel to deliver the medication.

The needle cap 158 is removed before syringe use. The needle cap 158 defines an outer cylindrical portion 160 that surrounds at least a portion of the needle guard, and an inner cylindrical needle holder 162 that surrounds the hypodermic needle. The needle holder 162 may function to hold the hypodermic needle during coupling with the Luer-lok of the barrel.

FIGS. 13-22 detail the sequential steps of readying, loading and administering an injection utilizing injection device 100. First, referring to FIG. 13, with the safety cap removed, the plunger lock 150 is moved to a predetermined starting position at the end of the grip 128 opposite the barrel, thereby allowing the plunger assembly to move freely relative to the barrel. Next, referring to FIG. 14, the user grips the grip 128, resting the top of the hand firmly against the underside of the grip flange 138 and placing the thumb against the underside of the barrel flange in order to push the barrel 102 in the direction away from the plunger to introduce air into the reservoir. Next, referring to FIG. 15, the user aligns the vial with the needle guard flange. Next, referring to FIG. 16, the user pushes the injection device or vial until the needle penetrates the vial and the "-0-" or equivalent zero dosage shows through the dosage window 132. The plunger is then withdrawn from the barrel 102 to fill the reservoir to the desired dosage amount that appears through the dosage window 132.

Figure 17:
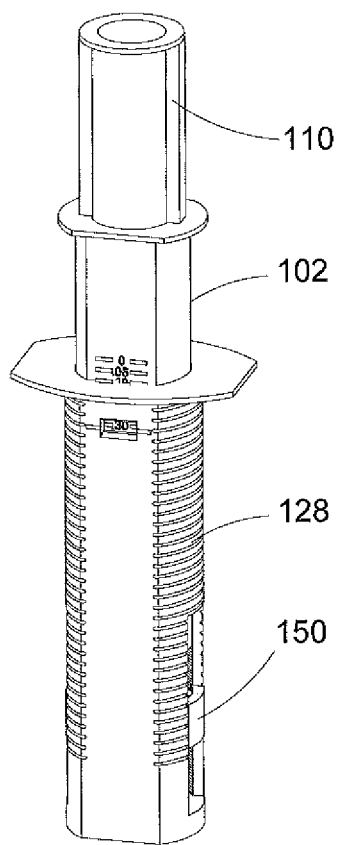
FIG. 17 shows the device of FIG. 1 loaded with a predetermined dosage of medication and with the plunger lock in the operative position.
Figure 18:
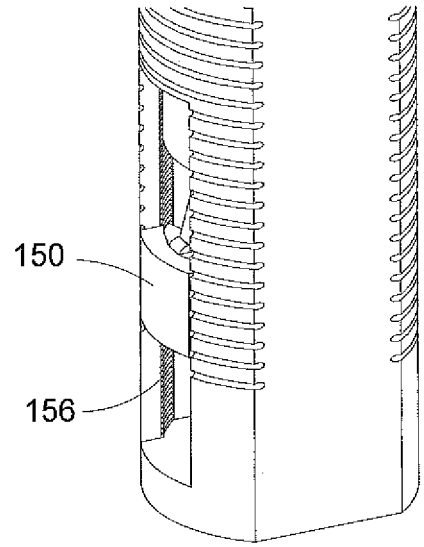
FIG. 18 is a detailed view of the plunger lock.
Figure 19:
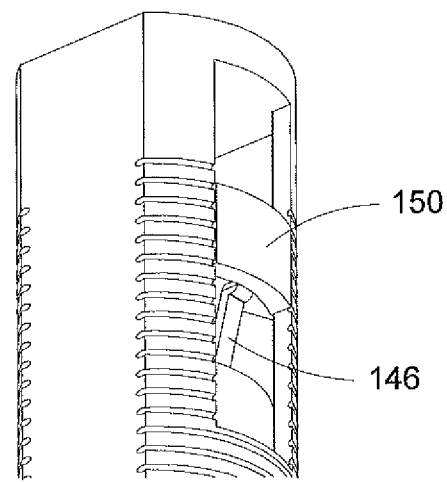
FIG. 19 is a detailed view of the plunger lock and plunger stop engagement.
Figure 23:
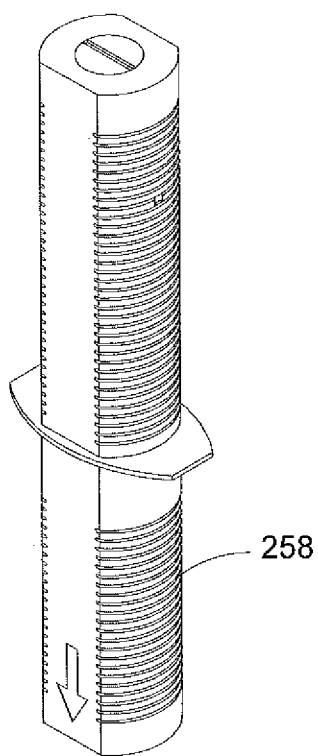
FIG. 23 is an isometric view of an injection device according to a second embodiment of the invention.
Figure 24:
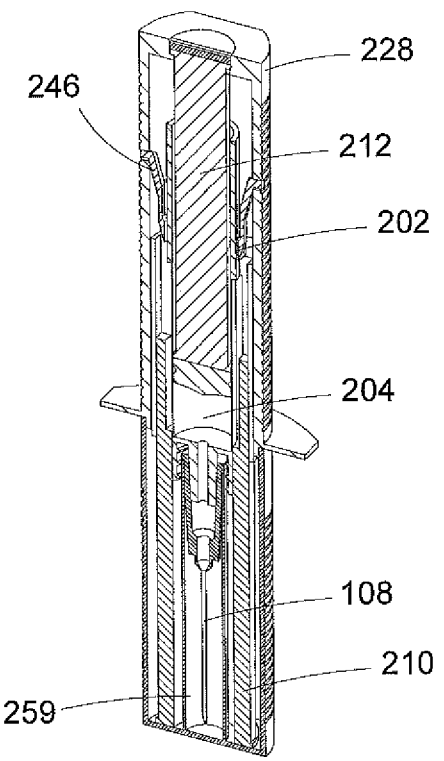
FIG. 24 is a longitudinal sectional view through the device of FIG. 23.
Figure 25:
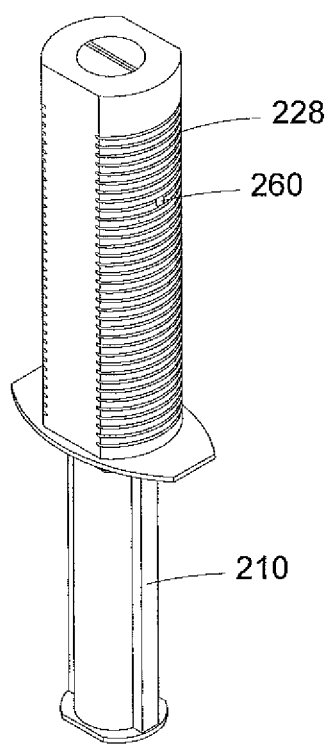
FIG. 25 shows the device of FIG. 23 with the safety cap removed.
Figure 26:
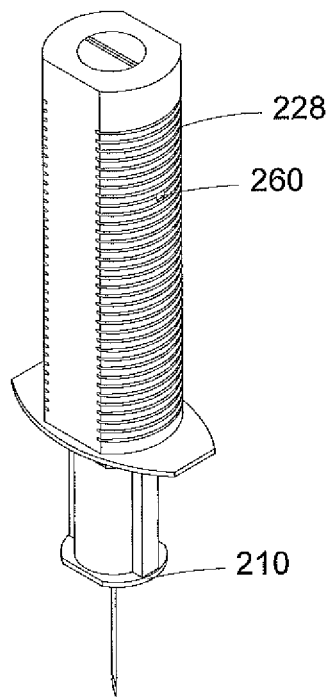
FIG. 26 shows the device of FIG. 23 with the needle guard partially retracted.
Figure 27:
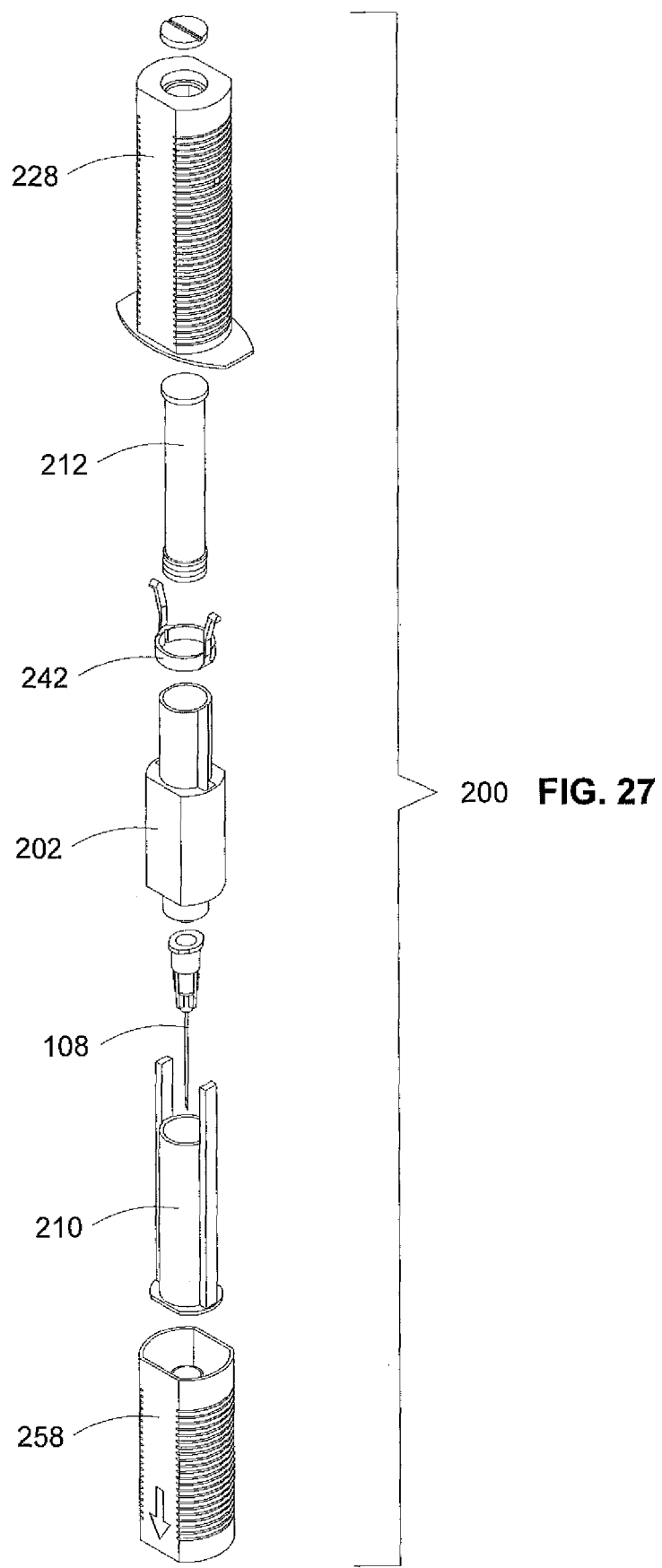
FIG. 27 is an exploded view of the device of FIG. 23.
Figure 28:
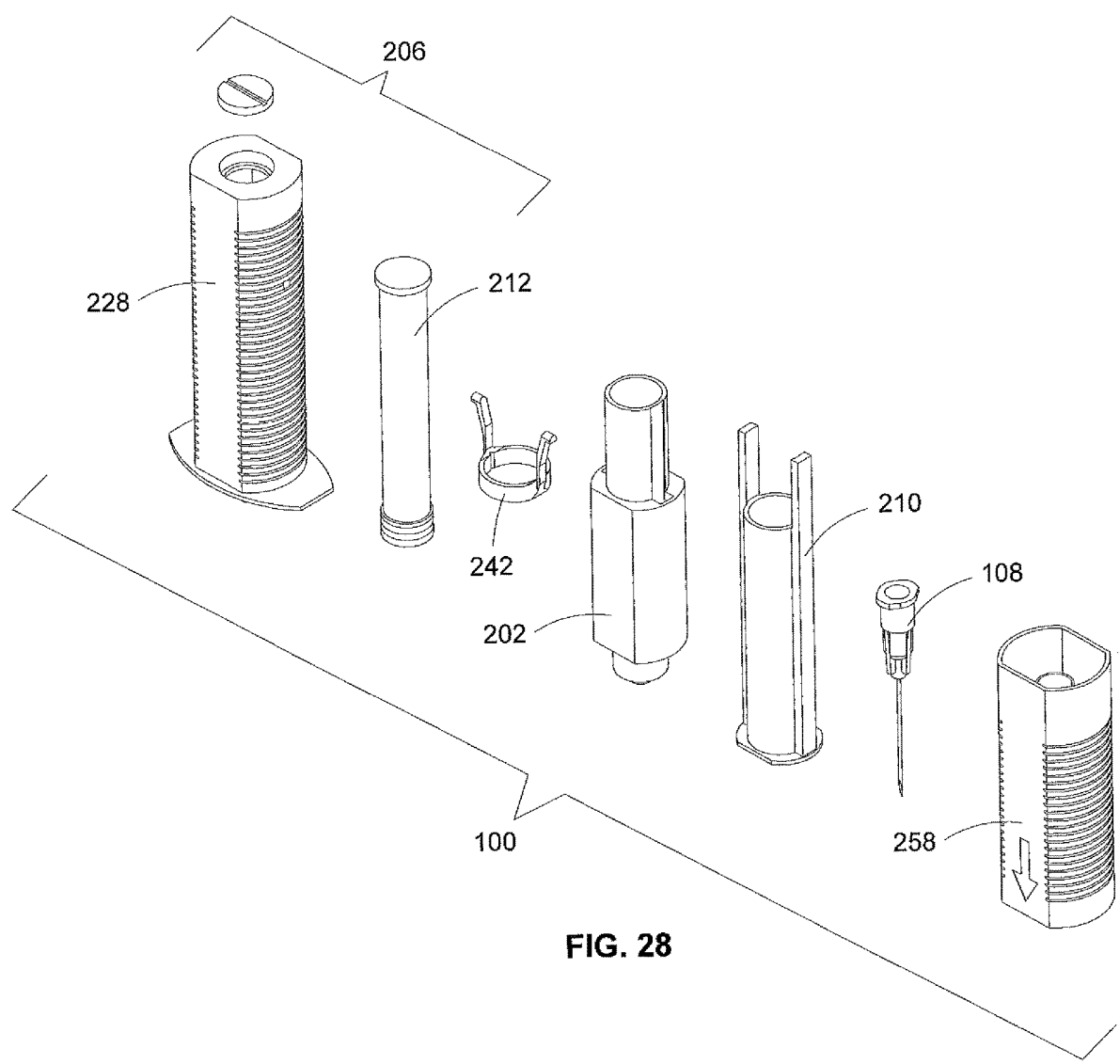
FIG. 28 is another exploded view of the device of FIG. 23.
Figure 29:
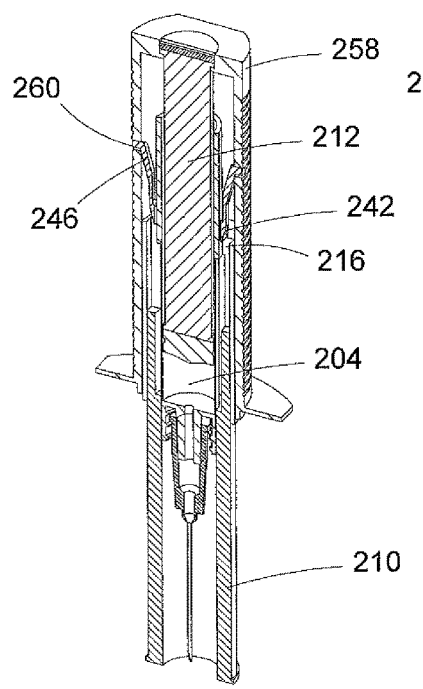
FIG. 29 is a sectional view through the device of FIG. 23 showing the device loaded and ready for use.
Figure 30:
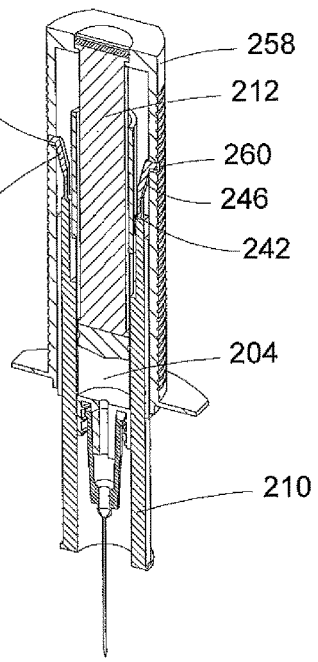
FIG. 30 is a sectional view through the device of FIG. 23 showing the needle guard partially retracted and the plunger locked.
Figure 31:
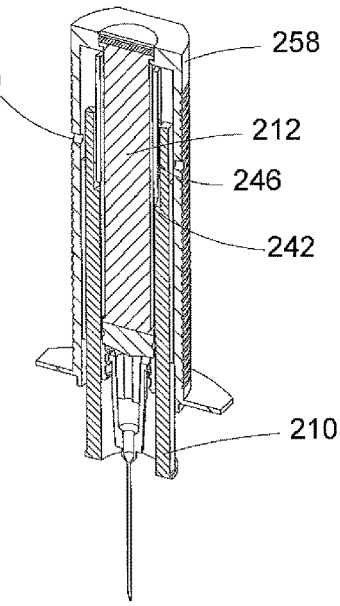
FIG. 31 is a sectional view through the device of FIG. 23 showing the needle guard fully retracted and the plunger released.
Figure 34:
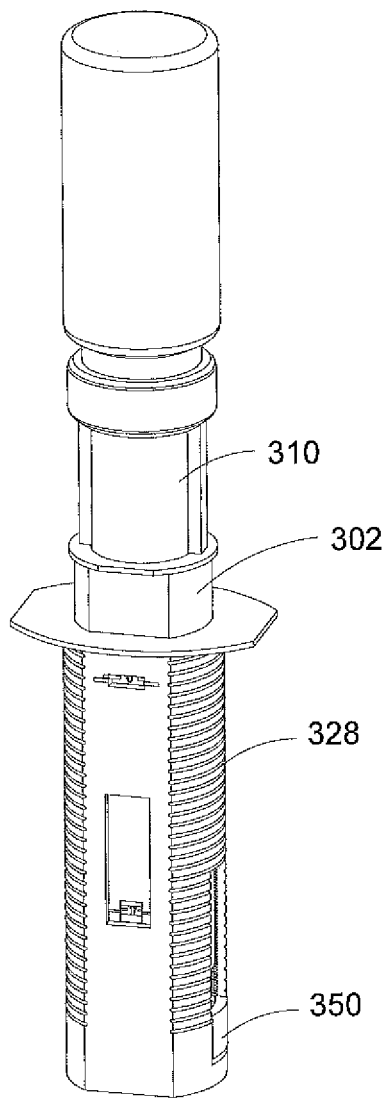
FIG. 34 shows the vial aligned with the needle guard.
Figure 35:
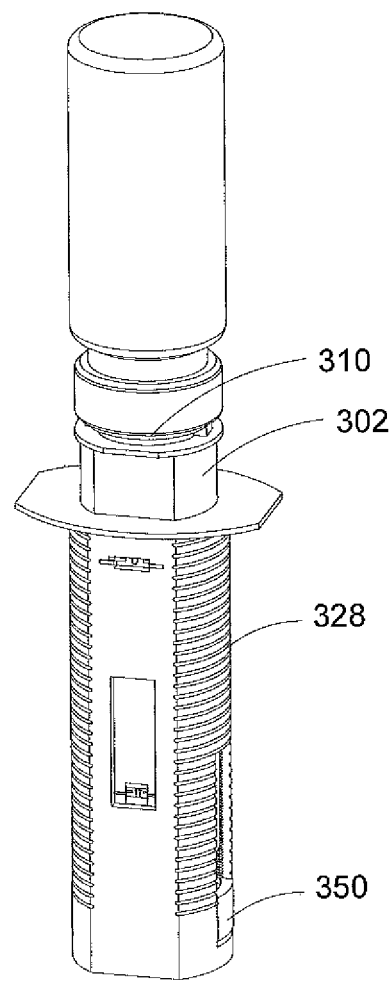
FIG. 35 shows the needle inserted into the vial.
Figure 39:
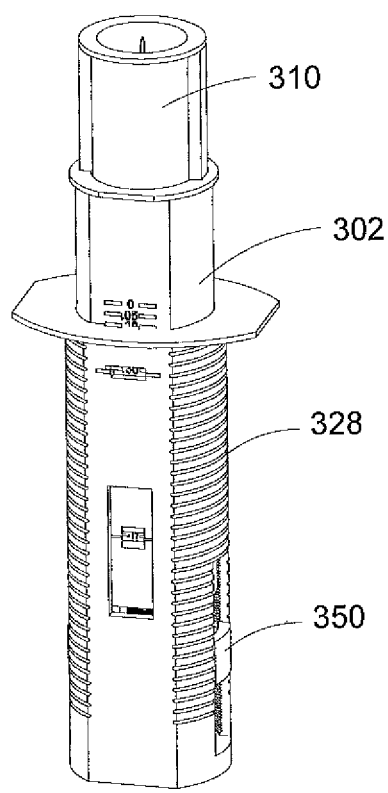
FIG. 39 shows the needle depth setting of the device.
Figure 40:
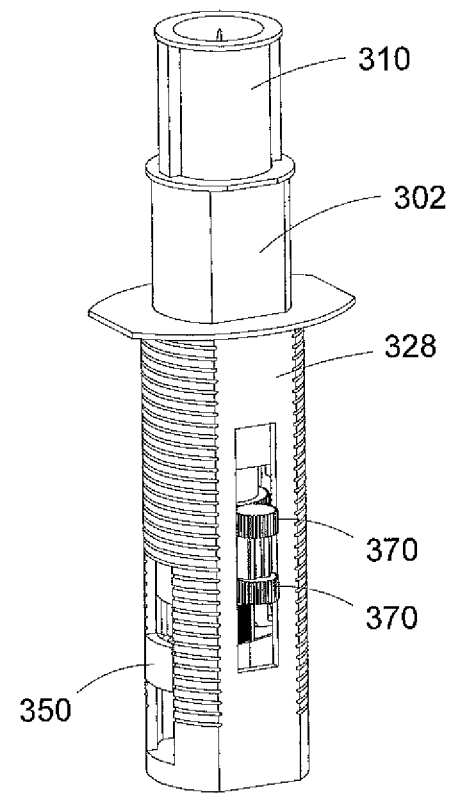
FIG. 40 shows the needle depth adjuster.
Figure 41:
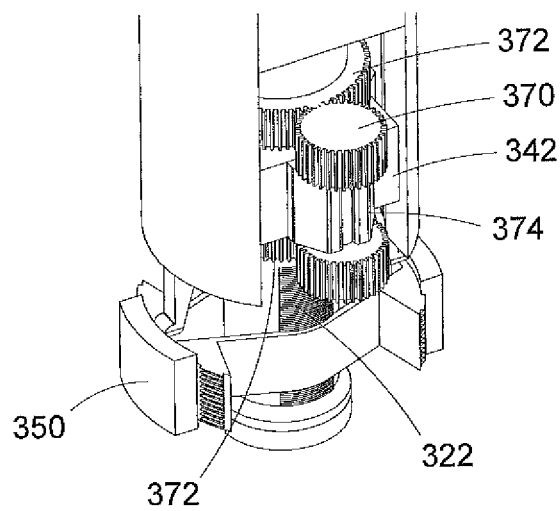
FIG. 41 is a detailed view of the needle depth adjuster.
Figure 42:
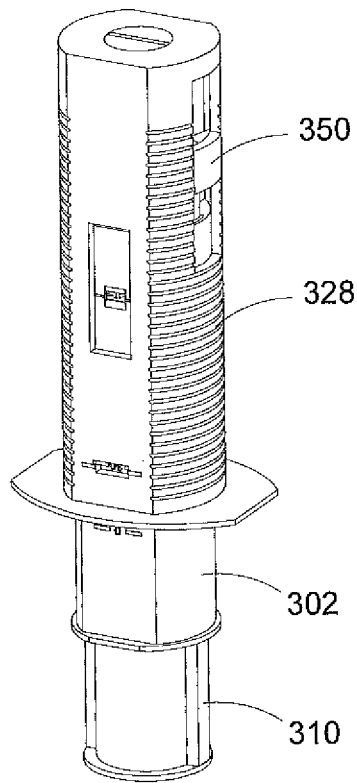
FIG. 42 shows the device of FIG. 32 loaded and set to a predetermined needle depth.
Figure 43:
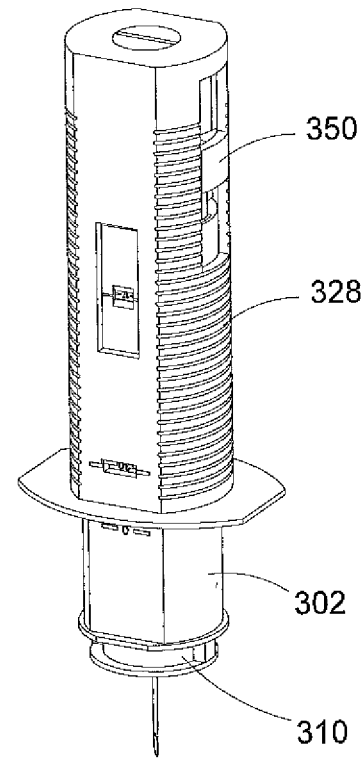
FIG. 43 shows the needle guard retracted and the plunger in the starting position.
Figure 44:
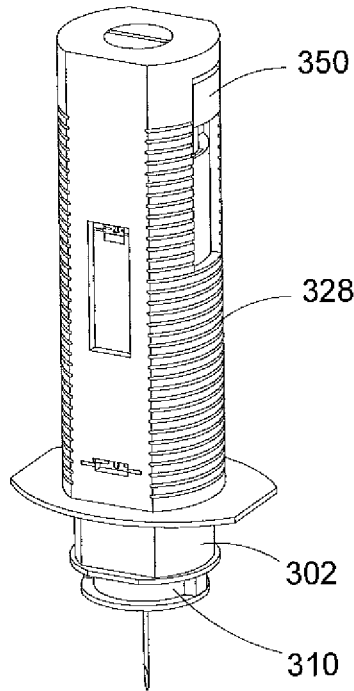
FIG. 44 shows the needle guard retracted and the plunger fully depressed.
Figure 45:
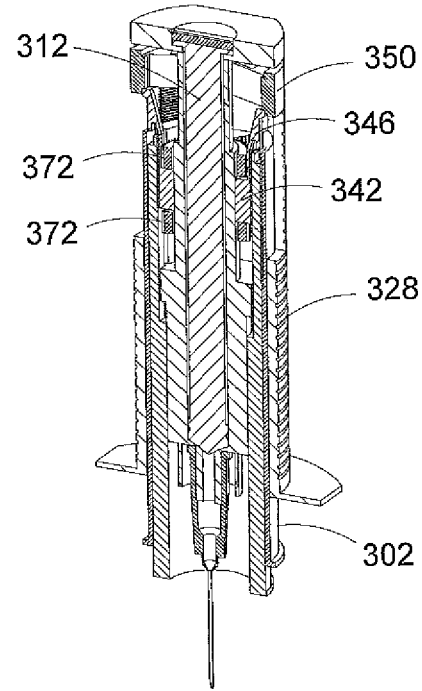
FIG. 45 is a sectional view through the device showing plunger release.
Figure 46:
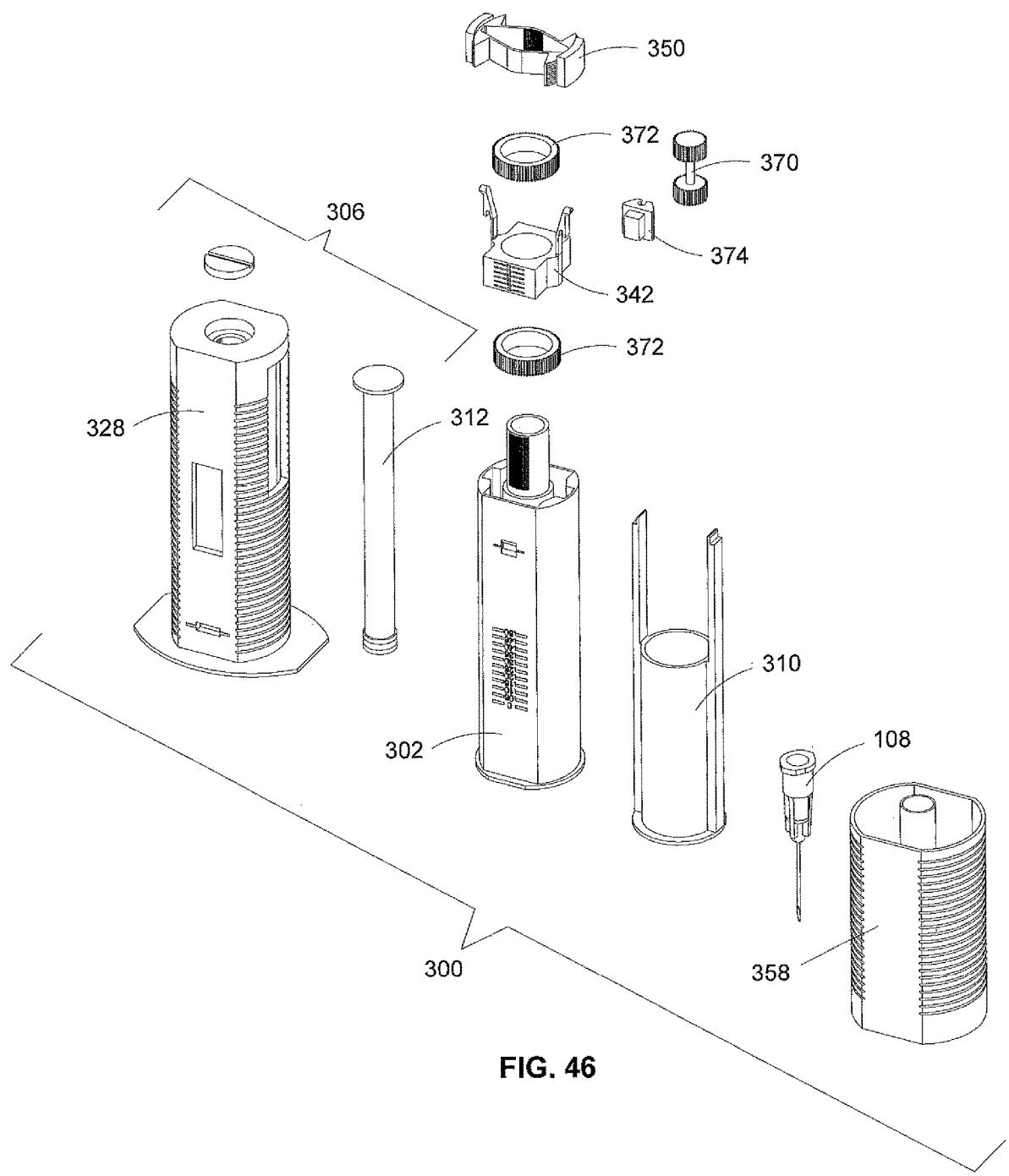
FIG. 46 is an exploded view of the device of FIG. 32.
Figure 47:
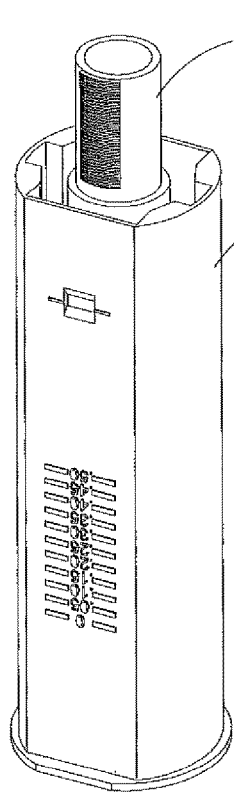
FIG. 47 is an isometric view of the barrel of the device of FIG. 32.
Figure 48:
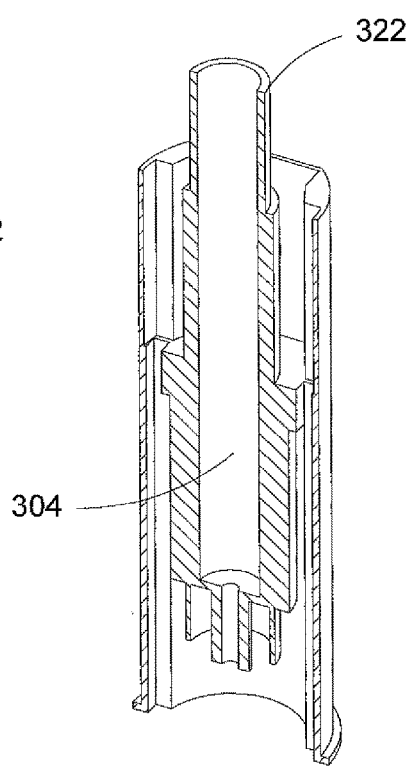
FIG. 48 is a longitudinal sectional view through the barrel.
Figure 49:
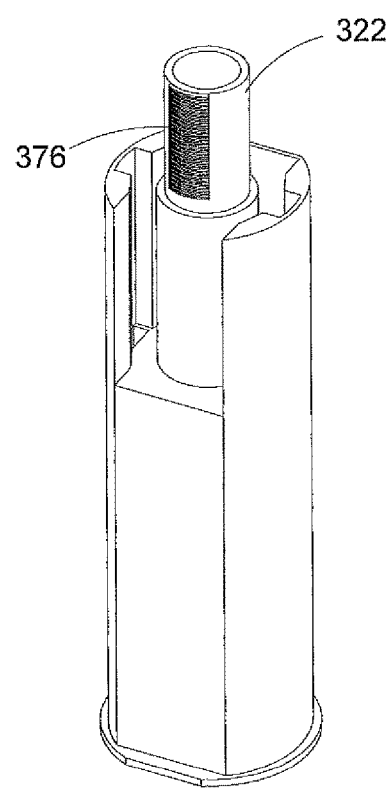
FIG. 49 is a cutaway view of the barrel of FIG. 47.
Figure 50:
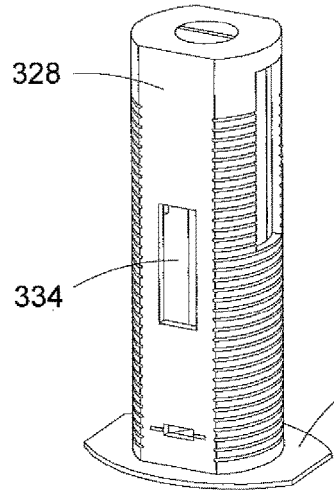
FIG. 50 is an isometric view of the plunger assembly of the device of FIG. 32.
Figure 51:
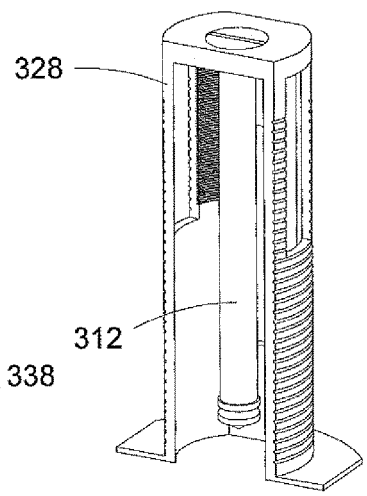
FIG. 51 is a cutaway view through the plunger assembly.
Figure 52:
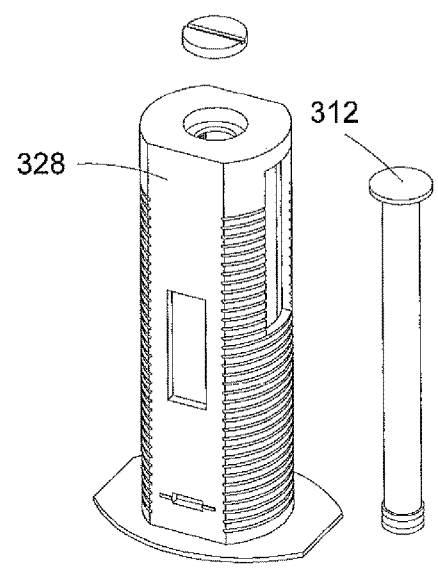
FIG. 52 is an exploded view of the plunger assembly of FIG. 50.
Figure 53:
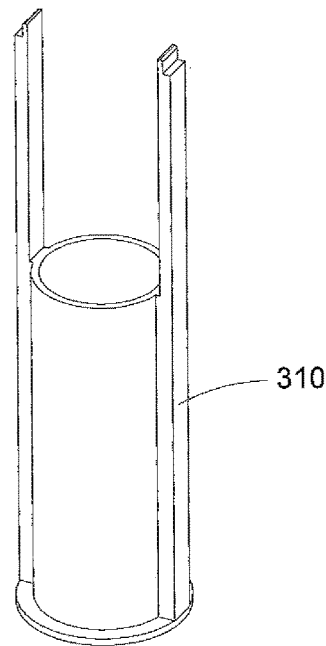
FIG. 53 is an isometric view of the needle guard of the device of FIG. 32.
Figure 54:
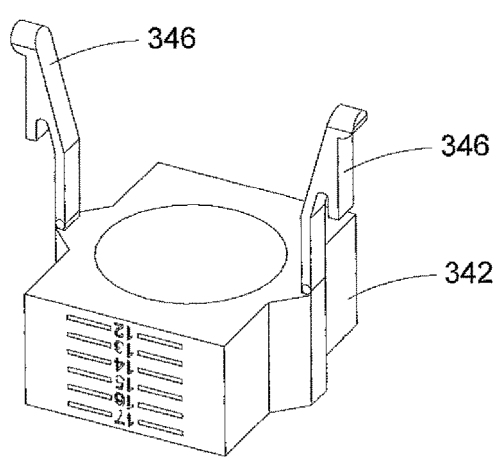
FIG. 54 is an isometric view of the plunger stop of the device of FIG. 32.
Figure 55:
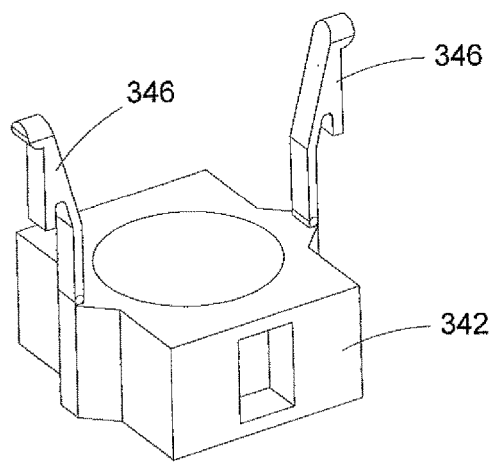
FIG. 55 is another isometric view of the plunger stop.
Figure 56:
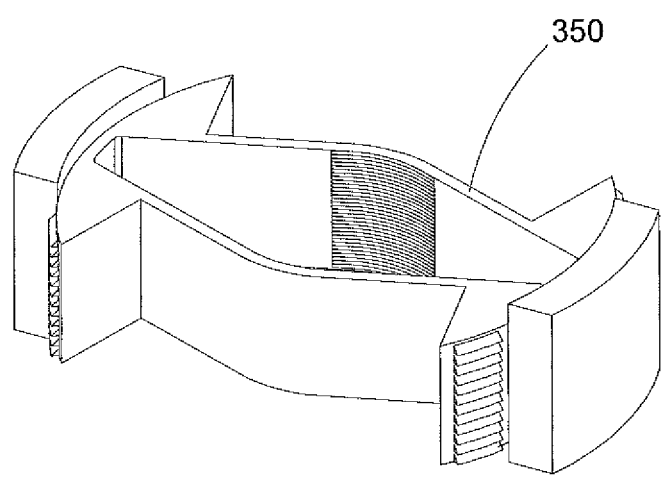
FIG. 56 is an isometric view of the plunger lock of the device of FIG. 32.
Figure 59:
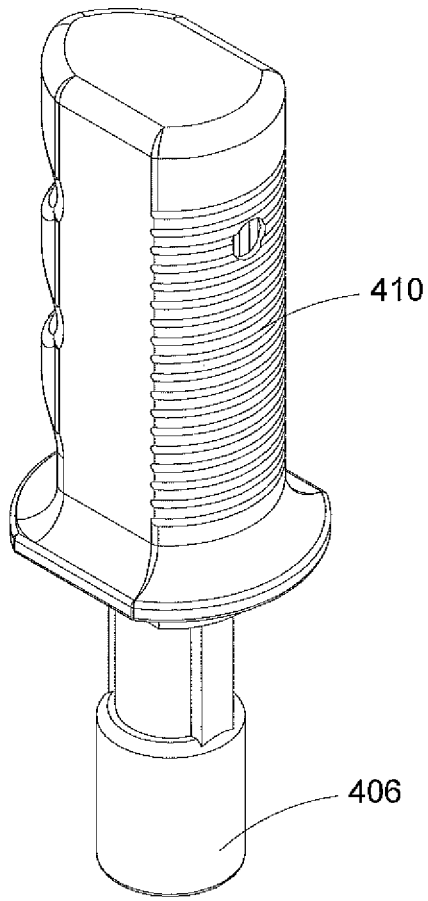
FIG. 59 shows the device of FIG. 57 loaded with a predetermined dosage and ready for use.
Figure 60:
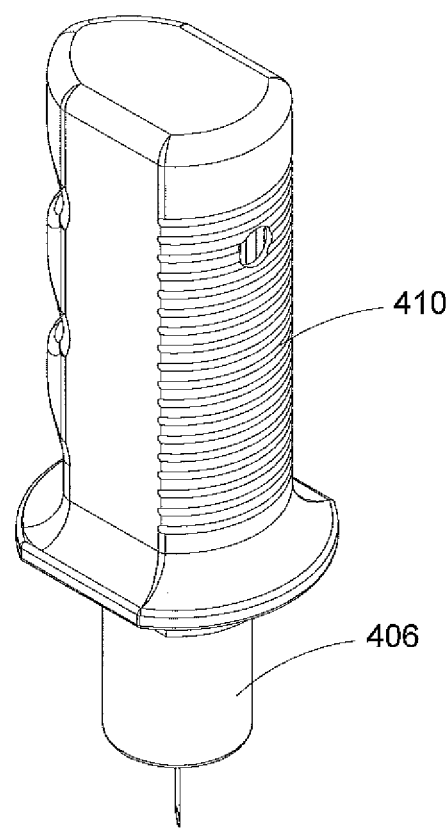
FIG. 60 shows the device of FIG. 57 with the needle guard partially retracted.
Figure 61:
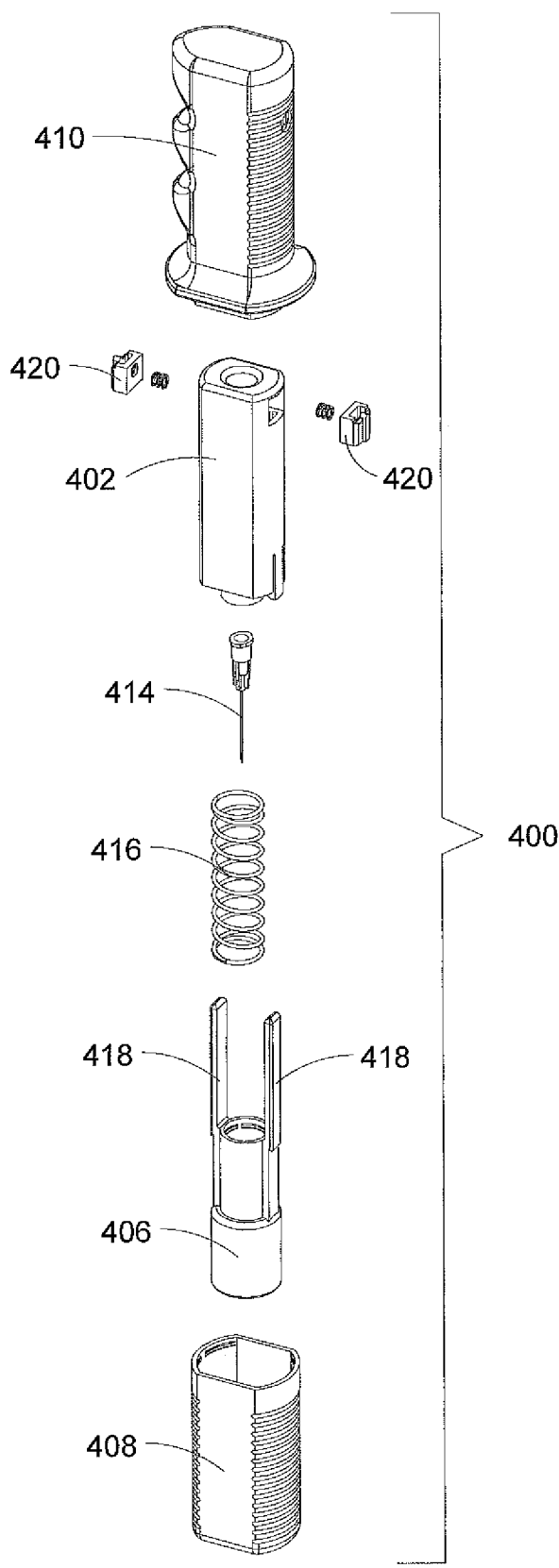
FIG. 61 is an exploded view of the device of FIG. 57.
Figure 62:
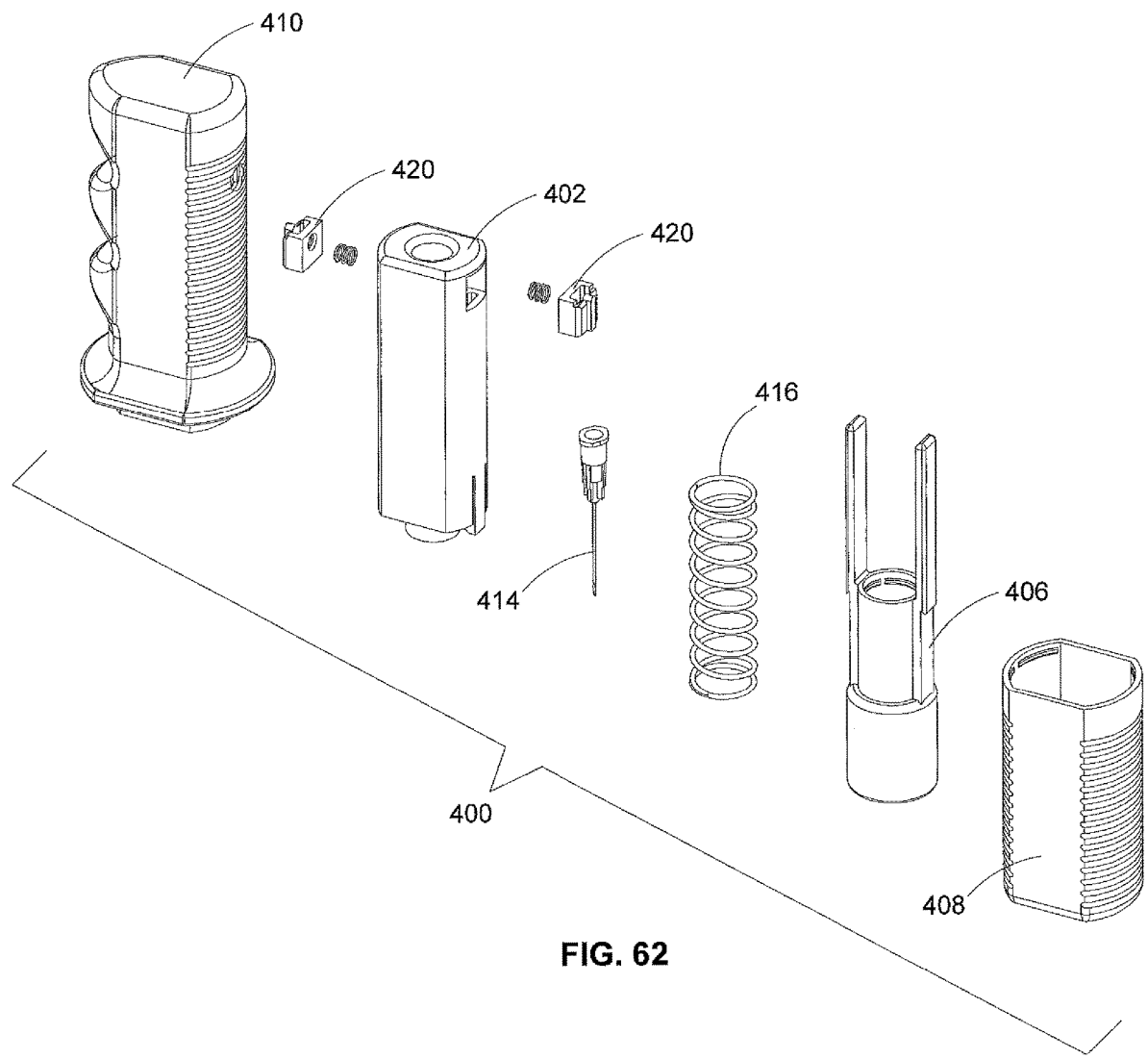
FIG. 62 is another exploded view of the device of FIG. 57.

Next, referring to FIG. 17, with the vial removed, the needle guard 110 is pulled out to a starting position and the plunger lock is "pinched" to compress the plunger lock radially to slide it into the operative "locked" position against the arms of the plunger stop. FIG. 18 details the plunger lock 150 engaging the teeth 156 on the inner surface of the grip. FIG. 19 details the plunger lock 150 engagement with the barrel and with the arms of the plunger stop.

Next, referring to FIG. 20, to administer the injection, the user grips the grip 128 seating the hand against the grip flange 138. The user applies a downward pressure on the grip and grip flange 138, thereby causing force between the injection site and needle guard 110 until the needle guard collapses and retracts upward into the barrel 102 a predetermined distance and the needle penetrates the injection site in response to forward pressure against the injection site. Referring to FIG. 21, as the needle guard 110 retracts, the needle guard rails 140 move into contact with the plunger stop arms 146. As the needle guard 110 continues to retract, the contact between the rails 140 and the arms 146 urges the arms radially inward, thereby releasing the plunger stop and allowing the plunger to move to complete the injection. Referring to FIG. 22, as part of the continuous injecting motion, the plunger continuous its "downward" motion to force the medication from the reservoir and out through the needle 108. Thus, needle guard retraction, needle insertion, plunger release, and plunger movement are sequentially performed in one continuous motion from force against the injection site, and plunger movement is stayed until the needle is fully inserted into the patient to a predetermined depth. After the injection is complete, the injection device may be discarded or reused after sterilizing the device and replacing the needle.

Referring to FIGS. 23-31, a second embodiment of an injection device for administering a dosage of medication is shown generally at reference numeral 200. Like injection device 100, injection device 200 generally operates by way of user force and momentum to sequentially insert the needle, trigger release of the plunger, and deliver the medication, in one continuous motion. Unlike injection device 100, in which the dosage can be adjusted, injection device 200 is pre-loaded with a predetermined dosage. The dosage can be customized based on weight, BMI and BSA, among other factors.

The injection device 200 includes a needle cap 258 removed prior to use. The needle cap 258 includes an inner cylindrical needle holder 259 that conceals the hypodermic needle 108. The needle cap 258 may be held in place, for example, by way of interference fit around a portion of the grip 228. Injection device 200 generally includes a barrel 202 defining an internal reservoir 204 containing a predetermined volume of medication, a plunger assembly 206 axially movable relative to the barrel to force the medication from the reservoir, a hypodermic needle 108 for delivering the medication intramuscularly, subcutaneously, or other route, and a retractable needle guard 210 for releasing the plunger assembly 206 to allow axial movement of the plunger relative to the barrel.

The barrel 202 may be a unitary or multi-piece body. The hypodermic needle 108 attaches to one end of the barrel 202, and the opposing end of the barrel is open to receive an internal plunger 212 of the plunger assembly 206 therein. An airtight seal is provided between the plunger 212 and the reservoir 204 such that the pre-loaded medication is forced through the needle as the plunger moves axially in the direction of the barrel 202. A portion of the barrel 202 has a generally cylindrical cross-section with diametrically opposed flat sides, which correspond in shape to the overlying grip 228 to prevent rotation therebetween when axially overlapped. The end of the reservoir adjacent the needle, i.e., the interface between the reservoir and needle, may be sealed with a foil or like seal that ruptures in response to the initial plunger movement and/or consequential pressure build-up in the reservoir. The rupture of the seal allows the medication to flow from the reservoir 204 to the needle.

In response to predetermined pressure against the injection site, the needle guard 210 rapidly retracts into the barrel 202. The barrel 202 defines an annular, internal space 216 for receiving the cylindrical body of the retracting needle guard 210, and diametrically opposed guide channels 218 for receiving and aligning the corresponding guide rails 240 extending from the needle guard body. The plunger stop 242 positioned around the axially extending stem 222 of the barrel 202 includes diametrically opposed arms 246 extending in the direction of the top of the grip 228. In use, the arms 246 are resiliently deformable and biased radially outward such that when the needle guard 210 is extended the ends of the arms engage within corresponding slots 260 thru the grip 228 to prevent axial movement of the plunger 212 relative to the barrel 202. When the needle guard 210 is retracted into the barrel 202 a sufficient distance, the needle guard urges the arms 246 radially inward out of engagement with the grip slots 260 such that the rails 240 can pass beyond the arms allowing the grip 228 to continue its motion in the direction of the injection site, thereby allowing the medication to be delivered. Features 260 facilitate gripping and handling.

Referring to FIGS. 32-56, a third embodiment of an injection device for administering a dosage of medication is shown generally at reference numeral 300. Injection device 300 operates much like injection devices 100 and 200, with the added functionality of adjustable needle length. It is should be understood that the adjustable needle length functionality may be added to one or more of injection devices 100 and 200 for the added benefit of patient customization, among other advantages.

Grip 328 includes a dosage window 332 through which the set dosage is indicated, and a needle depth window 334 through which the needle depth is indicated, for example, in units of millimeters. FIG. 32 shows the injection device 100 with the needle cap 358 installed, thereby concealing the underlying needle and preventing contamination. FIG. 33 shows the injection device in the "starting position," with the dosage set to "-0-", the plunger lock 350 disengaged allowing the plunger assembly 306 to move freely, and with the minimum needle depth set. Vial or ampoule alignment and plunger lock operation work in the same manner described above with reference to injection device 100.

The needle depth may be adjusted to change the depth of needle penetration. Depth of penetration is controlled by adjusting the point at which the needle guard 310 engages the plunger stop 342 to trigger the release of the plunger 312, and the adjustment is actuated by rotating a dial 370 accessible through the flat face of the grip 328 opposite the face including the dosage and needle depth indication windows. The dial 370 is part of an assembly also including one or more dial nuts 372 threaded onto the plunger stem 322. The dial 370 and one or more dial nuts 372 are meshed gears, wherein rotational motion of the dial 370 causes rotational motion of the one or more dial nuts 372. When turned, the one or more dial nuts 372 force the plunger stop 342 up or down the plunger stem 322 depending on the desired needle depth. In the embodiment shown, the dial assembly includes upper and lower dial nuts 372 positioned vertically above and below the plunger stop 342, and the dial 370 is held in a meshed arrangement with the dial nuts 372 by way of a dial holder 374 positioned adjacent a side of the plunger stop 342. With the dosage and needle depth set, the injection device 300 operates to deliver the dedication similar to injection device 100.

The barrel 302 generally includes the reservoir 304 for holding the medication, the stem 322 for locating the plunger stop 342, and the various guides and chambers for locating and guiding the retractable needle guard 310. Teeth on the stem 322 serve to grip the barrel 302 to prevent the plunger from pulling out of the barrel once the medication has been loaded and the plunger lock set to the predetermined dosage amount for the injection. External threads 376 on the stem 322 engage the internal threading on the one or more dial nuts 372 to adjust the needle depth in response to rotational movement of the dial 370. The grip flange 338 serves as a palm rest during the injecting motion.

The plunger stop 342 includes resilient arms 346 for engaging the plunger lock 350 (see FIG. 56) to prevent the plunger 312 from advancing into the reservoir 304 until released. Needle depth indicia may be located on a face of the plunger stop visible through the needle depth window 334. A slot is provided on one face of the dial for attaching the dial holder.

Referring to FIGS. 57-65, a fourth embodiment of an injection device for administering a dosage of epinephrine or other critical care injection is shown generally at reference numeral 400. Injection device 400 generally includes a barrel 402, plunger assembly 404, needle guard 406 and removable safety cap 408. As best shown in FIG. 58, the grip 410 and internal plunger 412 may be integrally formed, and the grip 410 may have a pistol grip shape to facilitate gripping.

The needle guard 406 is biased in the direction concealing the hypodermic needle 414. Optional helical spring 416 may be maintained between the needle guard 406 and the end of the barrel 402, requiring a small amount of force to overcome the spring force to retract the needle guard into the barrel. In an alternative embodiment, a resistance band 422 may be positioned surrounding the end of the barrel between the outer surface of the barrel and inner surface of the needle guard 406. The resistance band resists movement of the needle guard 406 relative to the barrel 402, requiring a predetermined degree of force to initiate retraction movement of the needle guard into the barrel. The helical spring 416 may be optionally included to provide smooth movement of the needle guard 406 relative to the barrel 402 throughout its range of movement. In one particular embodiment, both a resistance band and helical spring may be utilized, with the former resisting initial needle guard movement until a predetermined threshold resistance force is overcome, and the later providing smooth needle guard movement thereafter and biasing force in the direction concealing the needle.

A pair of axially extending spaced arms 418 of the needle guard 406 travel along the inner surface of the barrel 402. As the needle guard 406 is retracted into the barrel 402, the ends of the arms 418 engage a pair of spaced locks 420 to drive them radial inward to unlock the plunger assembly 404 from the barrel, thereby allowing the plunger 412 to be axially advanced into the reservoir.

Figure 63:
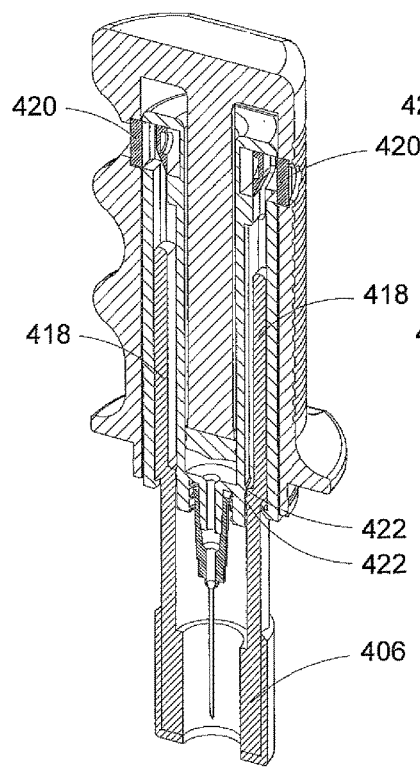
FIG. 63 is a sectional view through the device of FIG. 57 showing the needle guard extended and the plunger assembly locked.
Figure 64:
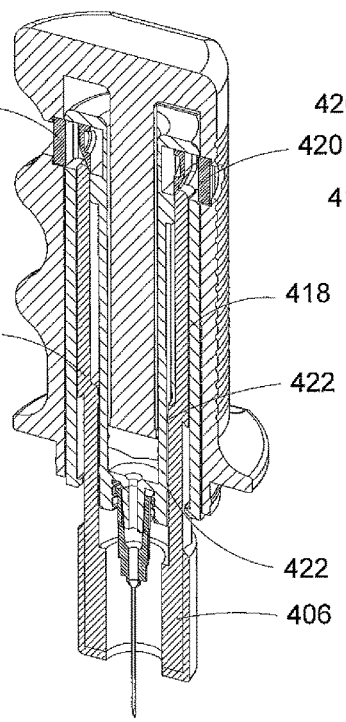
FIG. 64 is a sectional view through the device of FIG. 57 showing the needle guard partially retracted and the plunger assembly locked.
Figure 65:
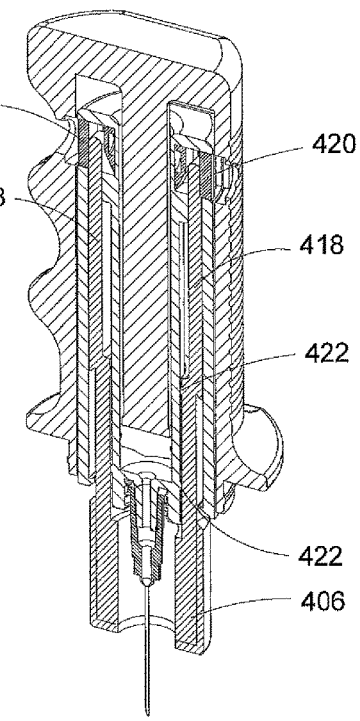
FIG. 65 is a sectional view through the device of FIG. 57 showing the plunger assembly unlocked.

The spaced locks 420 are arranged between the barrel 402 and inner surface of the grip 410 and are spring biased in the direction of the grip. Each lock 420 is ramped such that continued movement of the arms 418 in the direction of the locks causes the locks to be driven radially inward out of contact with the grip 410. In the "locked" position, each lock sits within a recess defined along the inner surface of the grip 410. In the "unlocked" position, the locks are driven from their respective recesses such that the plunger assembly 404 is free to move relative to the barrel 402. FIG. 63 shows the needle guard 406 fully extended and the locks 420 in their locked position. FIG. 64 shows the needle guard 406 partially retracted into the barrel and with with the arms 418 making initial contact with the locks 420. FIG. 65 shows the needle guard 406 retracted a sufficient amount such that the locks 420 are driven ort urged radially inward and out of contact with the grip 410.

Referring to FIGS. 66-74, a device for controlling actuation of a pre-filled syringe is shown generally at reference numeral 500. The device 500 generally operates to hold a syringe filled with a predetermined medication, i.e., a pre-filled syringe, and actuate the syringe to administer the predetermined medication in response to pressure against the injection site as discussed above in connection with the foregoing embodiments. In other words, the injection device 500 is momentum driven in that force against the injection site causes the needle guard of the device to partially retract into the barrel holder a predetermined distance to unlock the grip from the barrel holder to allow the grip to move in a direction of the injection site to advance the syringe plunger into the syringe barrel to deliver a dosage of the predetermined medication in one continuous motion.

The injection device 500 generally includes a barrel holder 502 having an internal axial passageway adapted to receive/hold a barrel 504 of the pre-filled syringe 506, a grip 508 slidably disposed over the barrel holder and adapted to engage a plunger 510 of the pre-filled syringe, and a needle guard 512 configured to partially retract into the barrel holder in response to force against the injection site to unlock the grip from the barrel holder. When locked, the grip 508 is fixed relative to the barrel holder 502 thereby preventing axial movement therebetween and consequently plunger movement relative to the syringe barrel. When unlocked, the grip 508 is able to move relative to the barrel holder 502 thereby pushing the plunger 510 in the direction of the barrel 504 to drive the predetermined medication out through the needle 514. FIG. 66 shows the injection device 500 locked and with a removable cover 516 installed, while FIG. 67 is a vertical sectional view through the injection device shown with the cover removed and with the grip 508 locked relative to the barrel holder 502.

Figure 68:
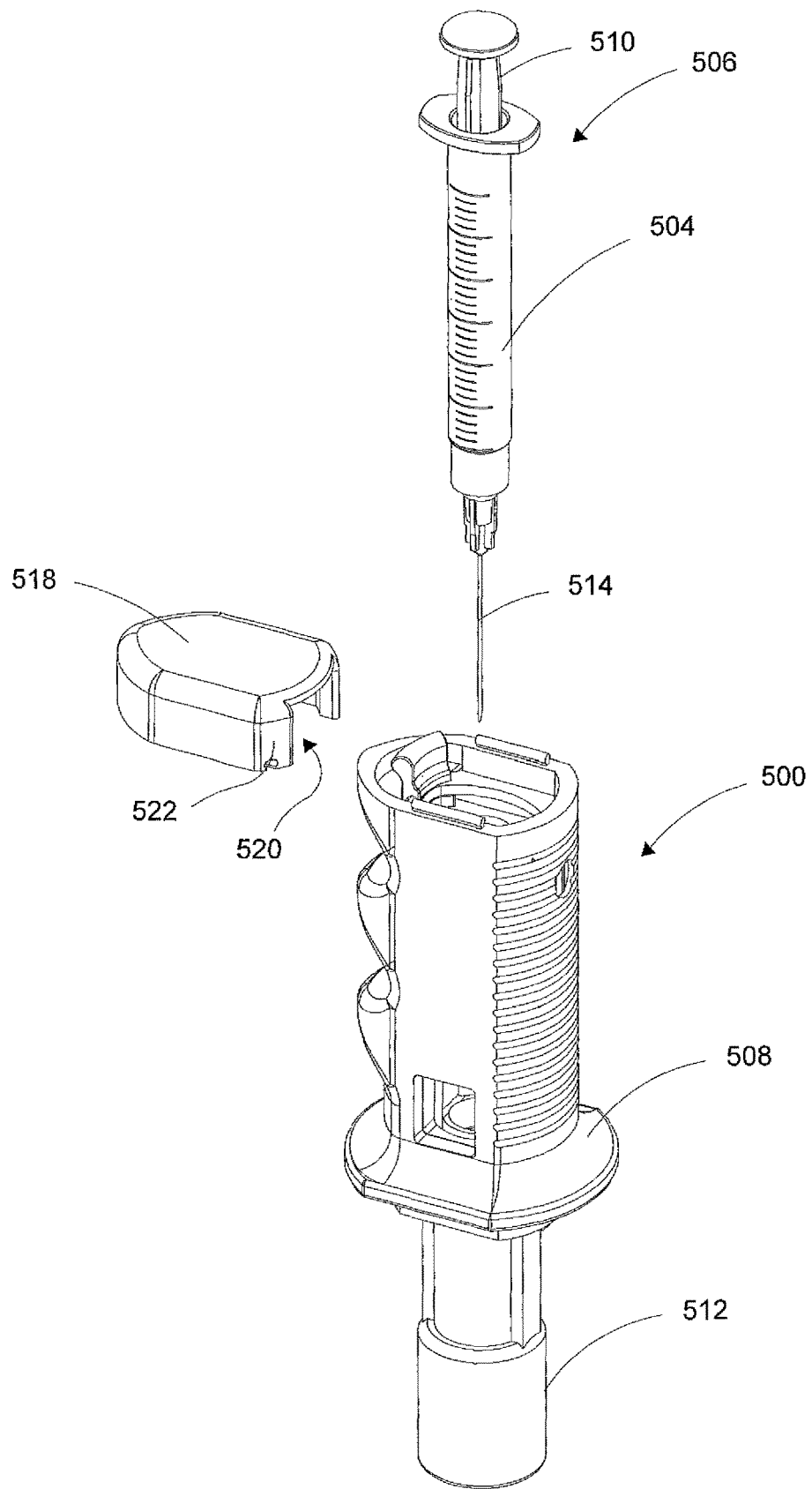
FIG. 68 shows the pre-filled syringe removed from the injection device.

The grip 508 has a removable cap 518 at one end thereof adapted to engage an end of the plunger 510 when installed on the grip. The removable cap 518 has an opening 520 through a sidewall 522 thereof for allowing the removable cap to slide over or past the end of the plunger 510 when installing the removable cap on the grip 508. As best shown in FIG. 68, the pre-filled syringe 506 is installed into the injection device 500 by first removing the cap 518 from the grip 508, next inserting the syringe 506 into the injection device, and finally replacing the cap 518 by sliding the cap onto the grip 508 from the side of the grip. The cap 518 and grip 508 can secure together through slide-lock engagement or equivalent manner of engagement. When the cap 518 is installed on the grip 508 the inner face of the end of the cap can directly contact the end of the enlarged head of the plunger.

Figure 69:
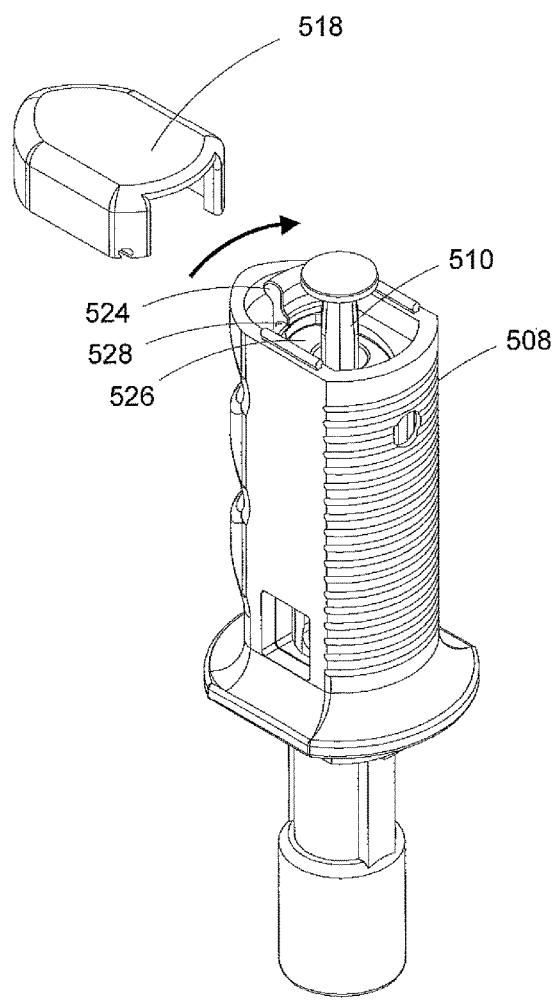
FIG. 69 shows a syringe lock in an unlocked position.
Figure 70:
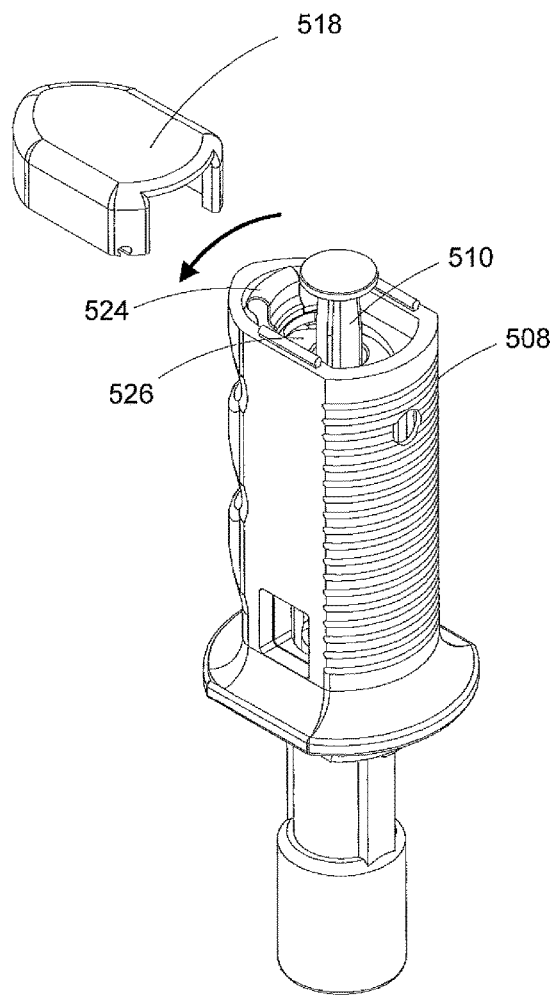
FIG. 70 shows the syringe lock in a locked position.

As best shown in FIGS. 69 and 70, the syringe barrel locks to the barrel holder 502 by way of a lock 524 positioned at one end of the barrel holder configured to lock the syringe barrel relative to the barrel holder. As shown, the finger flange 526 formed at the end of the syringe barrel sits within a recess formed in the end of the barrel holder 502. The lock 524, which slides along a rail 528 laterally adjacent the recess, defines a feature at one end that engages through a surrounding relationship one wing of the finger flange. More specifically, the lock 524 captures the wing of the finger flange between two arms thereof such that sliding the lock 524 along the rail 528 causes the finger flange to turn within the recess. The recess can be topped with a flange that allows the finger flange to pass thereunder when rotated to the locked position, thereby compressing the finger flange and locking the syringe barrel relative to the barrel holder. In the locked position, the syringe barrel is prevented from moving axially or rotationally relative to the barrel holder. The lock 524 is unlocked by sliding the lock in the opposite direction along the rail 528.

As best shown in FIG. 66, the injection device 500 can further include a window 530 through a sidewall thereof for viewing indicia 532 or fluid of the pre-filled syringe installed within the device to ensure proper installation among other purposes.

Figure 71:
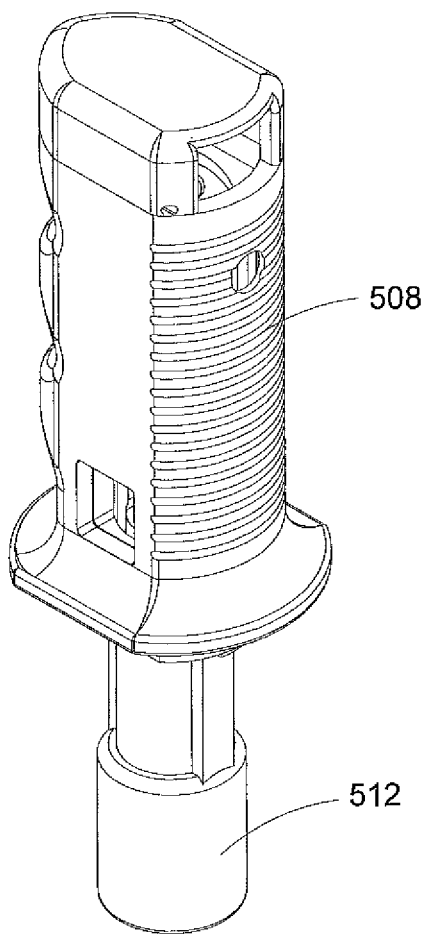
FIG. 71 shows the needle guard extended thereby concealing the needle.
Figure 72:
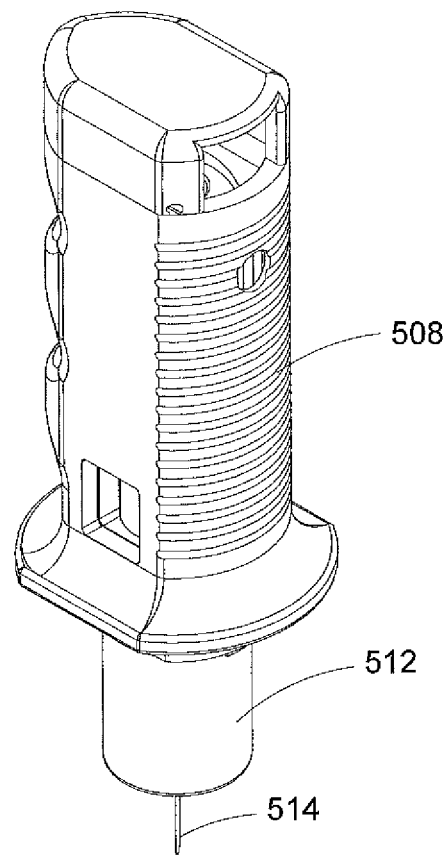
FIG. 72 shows the needle guard retracted and the plunger fully depressed.
Figure 73:
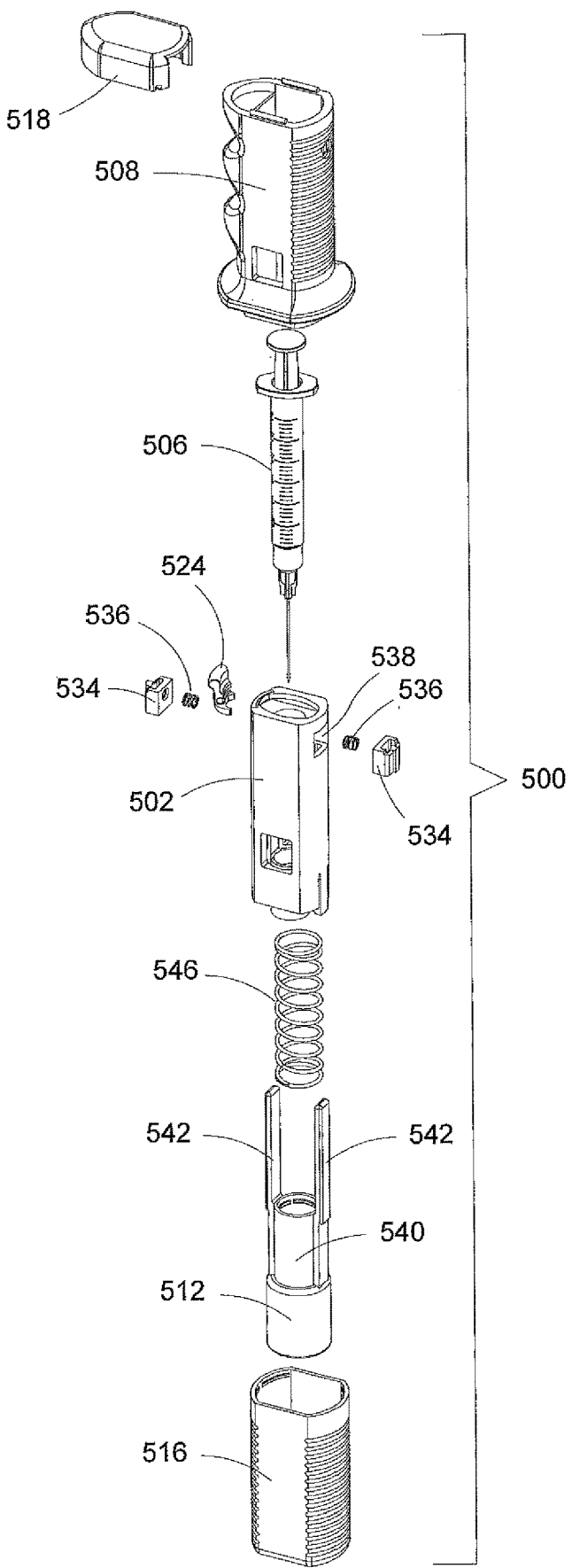
FIG. 73 is an exploded view of the injection device of FIG. 66.
Figure 74:
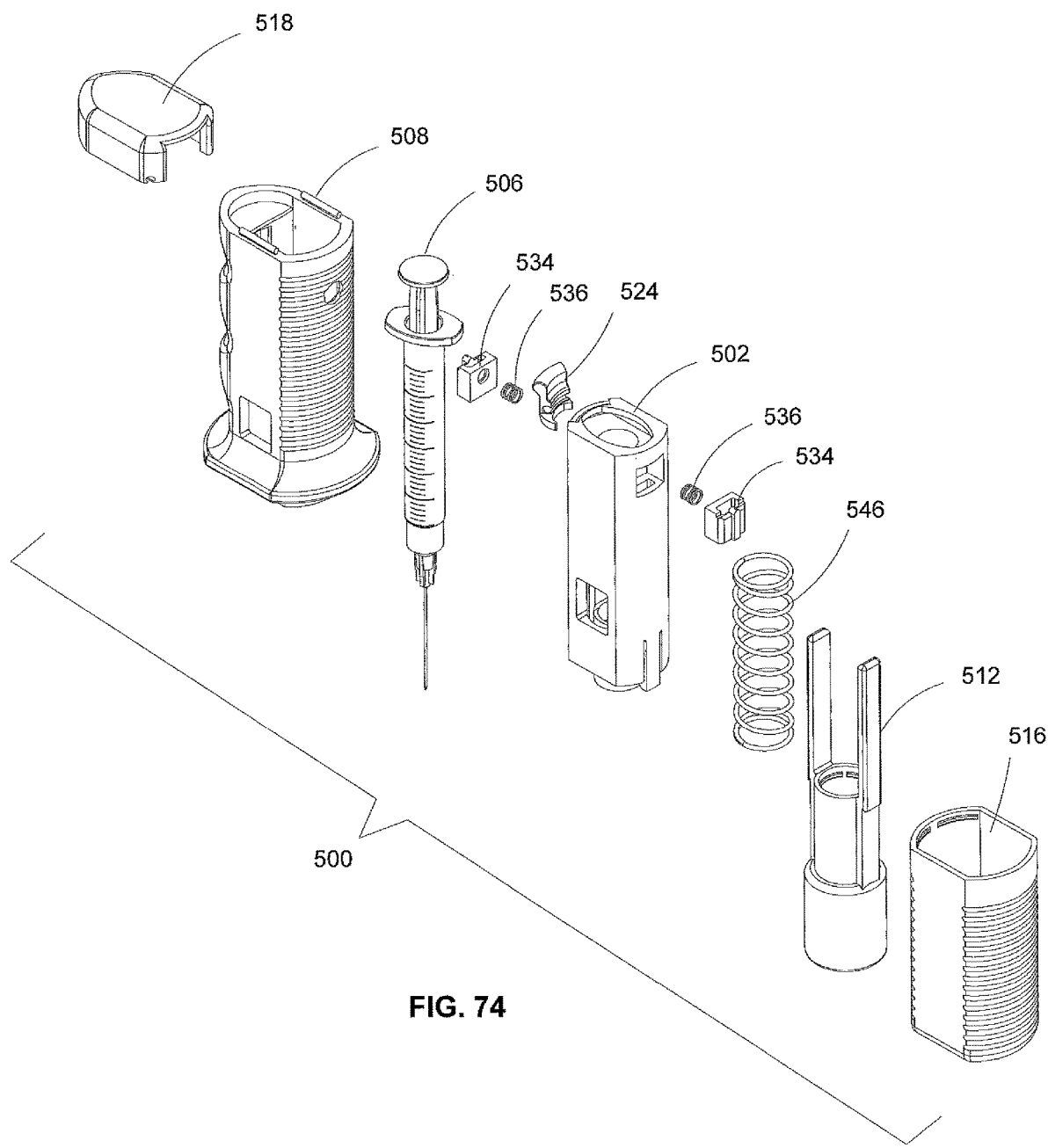
FIG. 74 is another exploded view of the injection device of FIG. 66.

Referring to FIGS. 71 and 72, the needle guard 512 partially retracts into the barrel holder in response to force against the injection site. FIG. 71 shows the needle guard 512 fully extended thereby concealing the needle. FIG. 72 shows the needle guard 512 partially retracted thereby exposing the needle. As can be seen referring to FIGS. 67, 73 and 74, grip 508 locking relative to the barrel holder 502 is achieved using a pair of diametrically opposed grip locks 534 outwardly biased in the direction away from the barrel holder 502. Biasing can be achieved using helical springs 536 or equivalent biasing member positioned inward of the grip locks 534. Each grip lock 534 seats within a dedicated opening or recess 538 defined in the sidewall of the barrel holder 502. When assembled, the grip locks 534 are biased outward to engage an inner surface of the grip 508 to lock the grip to the barrel holder 504, and are arranged to move out of contact with the grip 508 in response to contact with the needle guard 512 as the needle guard retracts into the barrel holder 502.

The needle guard 512 generally includes a cylindrical tubular body 540 having a pair of diametrically opposed arms 542 extending axially from one end of the cylindrical body in a direction of the grip 508. As the needle guard 512, and particularly the arms 542, retract into the barrel holder 502 a predetermined distance, the arms 542 contact the grip locks 534 thereby urging the grip locks inward and out of contact with the grip 508 to unlock the grip from the barrel holder 502 to permit axial movement therebetween. The arms 542 can be guided along elongate channels 544 within the interior of the barrel holder 502. A biasing member, such as a helical spring 546 can be disposed between one end of the barrel holder 502 and the needle guard 512 arranged to bias the needle guard in the direction away from the barrel holder, thereby requiring force against the injection site sufficient to overcome the spring force in order to allow the needle guard 512 to retract.

As in the above injection device embodiments, the injection device 500 can further include a needle depth adjustment mechanism including a plunger stop, a rotating dial accessible through a face of the grip, and one or more dial nuts adapted to thread on the plunger, the rotating dial adapted to mesh with the one or more dial nuts such that rotation of the dial rotates the one or more dial nuts to move the plunger stop up or down the plunger.

In any of the foregoing embodiments, the injection device may be included in a kit for increasing the effectiveness and safety of an injection. The kit may include the injection device marked with patient weight indicia, for example from 1-40 Kg for pediatric patients, or other patient characteristic indicia. The kit may further include one or more of a BMI card to assess a patient's BMI, correlating needles having a predetermined length to be used with the injection device, and a vial or other medicament container including a predetermined volume to support predetermined dosages.

The injection device or kit may be volumetrically predetermined for the medication and targeted patient class and/or patient segment dosage range. It is contemplated herein that the injection device may be filled by a user to a specific dosage, weight or other measurement, and the dosage stored and "locked" within the reservoir of the injection device for later use. The injection device may be pre-filled with the medicament to a predetermined volume to fulfill the administration requirements of a specific patient class, weight or other feature, as an example, pre-filled for a pediatric patient class of 40 Kg or under, or pre-filled for an infant weight class from 1-10 Kg. The injection device may be pre-filled with medication corresponding to a specific patient weight class or other patient characteristic dosage or dosage range, and predetermined needle length. The injection device may be pre-filled with a predetermined volume of medication to fulfill the administration requirements of a specific patient class, weight, BMI or other patient characteristic, and may also include a patient specific needle or other hypodermic delivery apparatus with packaging, labeling, color or text that would assist a user in a quick identification of the most optimal injection device for a particular patient.

The foregoing description provides embodiments of the invention by way of example only. It is envisioned that other embodiments may perform similar functions and/or achieve similar results. Any and all such equivalent embodiments and examples are within the scope of this disclosure.

What is claimed is:

1. An injection device, comprising:
a barrel holder having an axial passageway adapted to hold a barrel of a pre-filled syringe;
a grip slidably disposed over the barrel holder and adapted to engage a plunger of the pre-filled syringe, the grip including a removable cap installable at one end of the grip, the removable cap adapted to engage an end of the plunger upon installation of the removable cap on the grip, and the removable cap including an opening through a sidewall thereof allowing the removable cap to slide over the end of the plunger when installing the removable cap on the grip, the grip configured to lock to the barrel holder to prevent axial movement therebetween and unlock from the barrel holder to allow axial movement therebetween to drive axial movement of the plunger relative to the barrel;
a barrel lock at one end of the barrel holder for preventing relative movement between the barrel holder and the barrel of the pre-filled syringe when installed in the barrel holder, the barrel lock including a recess for receiving a finger flange, a rail adjacent the recess, and a lock slidable along the rail into or out of engagement with the finger flange; and
a needle guard configured to partially retract into the barrel holder in response to force against an injection site to unlock the grip from the barrel holder by urging inward at least one outwardly biased element engaging the grip.

2. The injection device of claim 1, wherein the barrel holder comprises a window through a sidewall thereof for viewing indicia or fluid of the pre-filled syringe.

3. The injection device of claim 1, further comprising grip locks disposed in openings through sidewalls of the barrel holder, the grip locks arranged to contact the grip to lock the grip to the barrel holder and move out of contact with the grip in response to contact with the needle guard to unlock the grip from the barrel holder.

4. The injection device of claim 3, wherein the grip locks are biased outward away from the barrel holder.

5. The injection device of claim 3, wherein the needle guard comprises a cylindrical body having a pair of diametrically opposed arms extending axially from one end of the cylindrical body in a direction of the grip, as the needle guard retracts into the barrel holder a predetermined distance the arms urging the grip locks inward out of contact with the grip to unlock the grip from the barrel holder to permit axial movement therebetween.

6. The injection device of claim 5, wherein the arms are guided along elongate channels within the barrel holder.

7. The injection device of claim 1, further comprising a biasing member disposed between the barrel holder and the needle guard arranged to bias the needle guard away from the barrel holder.

8. The injection device of claim 1, wherein the injection device is momentum driven in that force against the injection site causes the needle guard to retract into the barrel holder a predetermined distance to unlock the grip from the barrel holder to allow the grip to move in a direction of the injection site to advance the plunger in the barrel to deliver a dosage of predetermined medication in one continuous motion.

9. An injection device for actuating a pre-filled syringe, comprising:
a barrel holder having an axial passageway adapted to hold a barrel of the pre-filled syringe;
a grip movable relative to the barrel holder to move a plunger of the pre-filled syringe, the grip including a removable cap at one end thereof, the removable cap adapted to engage an end of the plunger upon installation of the removable cap at the one end of the grip, the grip configured to be locked to the barrel holder to prevent axial movement therebetween and unlocked from the barrel holder to permit axial movement therebetween;
a barrel lock at one end of the barrel holder for preventing relative movement between the barrel holder and the barrel of the pre-filled syringe when installed in the barrel holder, the barrel lock including a recess for receiving a finger flange, a rail adjacent the recess, and a lock slidable along the rail into or out of engagement with the finger flange; and
a needle guard arranged to retract into the barrel holder in response to force against an injection site to unlock the grip from the barrel holder by urging inward at least one outwardly biased element engaging the grip.

10. The injection device of claim 9, wherein the at least one outwardly biased element is disposed in openings through sidewalls of the barrel holder, the at least one outwardly biased element arranged to contact the grip to lock the grip to the barrel holder and move out of contact with the grip in response to contact with the needle guard to unlock the grip from the barrel holder, wherein the at least one outwardly biased element is biased laterally away from the barrel holder.

11. The injection device of claim 9, further comprising a biasing member disposed between the barrel holder and the needle guard arranged to bias the needle guard away from the barrel holder.

12. The injection device of claim 9, wherein the needle guard comprises a cylindrical body having a pair of diametrically opposed arms extending axially from one end thereof in a direction of the grip, as the needle guard retracts into the barrel holder a predetermined distance the arms urging the at least one outwardly biased element inward out of contact with the grip to unlock the grip from the barrel holder to permit axial movement therebetween, wherein the arms are guided along elongate channels within the barrel holder.

* * * * *